US008858604B2

(12) United States Patent
Biyani et al.

(10) Patent No.: US 8,858,604 B2
(45) Date of Patent: Oct. 14, 2014

(54) CERVICAL PLATE ASSEMBLY

(75) Inventors: Ashok Biyani, Sylvania, OH (US);
Michael A. Rymer, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 13/616,852

(22) Filed: Sep. 14, 2012

(65) Prior Publication Data

US 2013/0012993 A1   Jan. 10, 2013

Related U.S. Application Data

(62) Division of application No. 12/536,699, filed on Aug. 6, 2009, now Pat. No. 8,287,574.

(60) Provisional application No. 61/086,653, filed on Aug. 6, 2008.

(51) Int. Cl.
*A61B 17/80* (2006.01)
*A61B 17/70* (2006.01)

(52) U.S. Cl.
CPC ......... *A61B 17/7059* (2013.01); *A61B 17/8042* (2013.01); *A61B 17/808* (2013.01); *A61B 17/8004* (2013.01); *A61B 17/8009* (2013.01); *A61B 17/8038* (2013.01)
USPC .......................................... 606/292; 606/295

(58) Field of Classification Search
USPC ................... 606/289, 292, 294–296
See application file for complete search history.

(56) References Cited

U.S. PATENT DOCUMENTS

| | | | |
|---|---|---|---|
| 5,964,762 A | 10/1999 | Biedermann et al. | |
| 6,306,139 B1 * | 10/2001 | Fuentes | 606/70 |
| 6,428,542 B1 | 8/2002 | Michelson | |
| 6,932,820 B2 | 8/2005 | Osman | |
| 7,074,221 B2 | 7/2006 | Michelson | |
| 7,214,226 B2 | 5/2007 | Alleyne | |
| 7,306,605 B2 | 12/2007 | Ross | |
| 7,318,825 B2 | 1/2008 | Butler et al. | |
| 7,399,174 B2 | 7/2008 | Deardurff et al. | |
| D581,055 S | 11/2008 | Mateyka | |
| 7,635,364 B2 | 12/2009 | Barrall et al. | |
| 7,635,366 B2 | 12/2009 | Abdou | |
| 7,641,675 B2 | 1/2010 | Lindemann et al. | |
| 7,645,295 B2 | 1/2010 | Osman | |
| 7,662,154 B2 * | 2/2010 | Ribeiro | 606/70 |
| 2002/0147450 A1 * | 10/2002 | LeHuec et al. | 606/61 |
| 2005/0043732 A1 | 2/2005 | Dalton | |
| 2007/0043369 A1 * | 2/2007 | Wallenstein et al. | 606/69 |

* cited by examiner

*Primary Examiner* — Andrew Yang
(74) *Attorney, Agent, or Firm* — MacMillan, Sobanski & Todd, LLC

(57) ABSTRACT

A cervical plate assembly facilitates the fusion of cervical vertebrae by quickly and easily causing the vertebrae to exert a preloading force against a bone graft interposed therebetween. A cervical plate assembly also facilitates the installation of the cervical plate assembly in an orthopedic surgical procedure by providing both a locking mechanism that positively retains one or more fasteners thereto and a viewing window that results in an unobstructed view of the vertebrae and the bone graft.

8 Claims, 28 Drawing Sheets

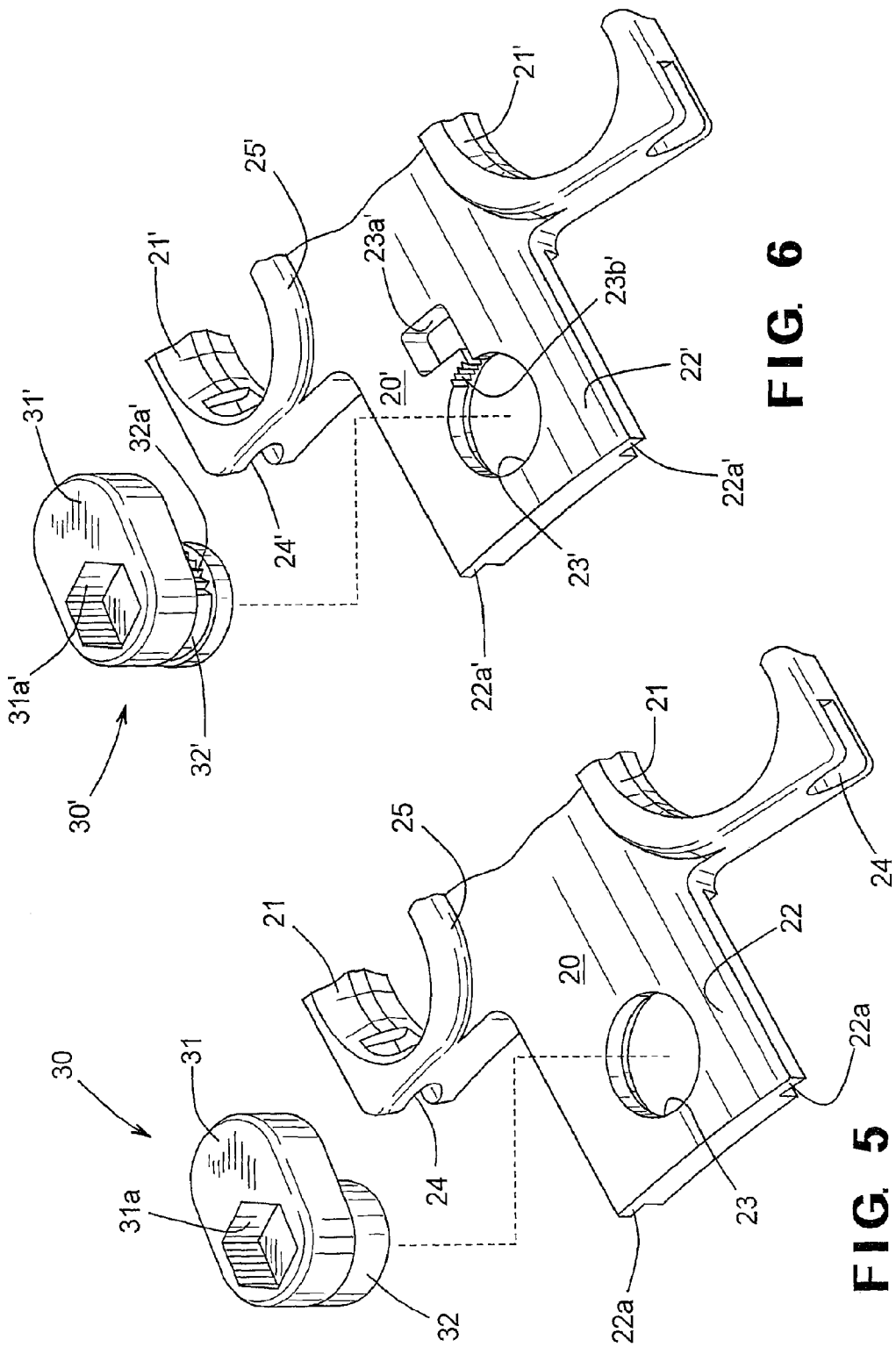

CERVICAL PLATE ASSEMBLY

CROSS-REFERENCE TO RELATED APPLICATIONS

This application claims the benefit of U.S. Provisional Application No. 61/086,653, filed Aug. 6, 2008, the disclosure of which is incorporated herein by reference. This application is also a divisional patent application of U.S. patent application Ser. No. 12/536,699, filed Aug. 6, 2009, the disclosure of which is also incorporated herein by reference.

STATEMENT REGARDING FEDERALLY SPONSORED RESEARCH OR DEVELOPMENT

Not applicable

BACKGROUND OF THE INVENTION

This invention relates in general to devices that facilitate the securement of selected bones of the human body to one another in surgical procedures. In particular, this invention relates to an improved structure for a cervical plate assembly that facilitates the fusion of two or more cervical vertebrae in an orthopedic surgical procedure by quickly and easily causing the vertebrae to exert a preloading force against a bone graft interposed therebetween. This invention also relates to an improved structure for a cervical plate assembly that facilitates the installation of the cervical plate assembly in an orthopedic surgical procedure by providing both a locking mechanism that positively retains one or more fasteners thereto and a viewing window that results in an unobstructed view of the vertebrae and the bone graft.

Many surgical procedures involve the securement of selected bones of the human body to one another. For example, when a spinal disc is removed from between two vertebrae in a spine (usually as the result of injury or degradation over time), a cervical spinal fusion procedure may be performed to secure the vertebrae together to prevent any relative movement from occurring therebetween. Such a cervical spinal fusion procedure typically involves the insertion of a bone graft in the space between the vertebrae that was previously occupied by the spinal disc. The bone graft fills the space left by the removed spinal disc and promotes the fusion of the vertebrae, a process that creates one continuous bone surface and eliminates motion at the fused joint.

After the bone graft has been inserted between the vertebrae, it is important to fix the spacing and alignment of such vertebrae relative to one another to allow the fusion process to occur. Such fixation is frequently accomplished by one or more cervical plates. A typical cervical plate is a rigid structure having first and second portions that are respectively secured to the two vertebrae after the bone graft has been inserted therebetween. Each of the first and second portions of the cervical plate is secured to its associated vertebra by one or more bone screws or other releasable fasteners. In this manner, the cervical plate rigidly engages the vertebrae to prevent any relative movement from occurring therebetween while the fusion process occurs.

A variety of cervical plate structures are known in the art and function satisfactorily. However, it is known that the fusion process can be facilitated by causing the vertebrae to exert a preloading force against the bone graft interposed therebetween. Thus, it would be desirable to provide an improved structure for a cervical plate assembly that facilitates the fusion of cervical vertebrae by quickly and easily causing the vertebrae to exert a preloading force against the bone graft interposed therebetween. It would also be desirable to provide an improved structure for a cervical plate assembly that facilitates the installation of the cervical plate assembly by providing both a locking mechanism that positively retains one or more fasteners thereto and a viewing window that results in an unobstructed view of the vertebrae and the bone graft.

SUMMARY OF THE INVENTION

This invention relates to an improved structure for a cervical plate assembly that facilitates the fusion of cervical vertebrae by quickly and easily causing the vertebrae to exert a preloading force against a bone graft interposed therebetween. This invention also relates to an improved structure for a cervical plate assembly that facilitates the installation of the cervical plate assembly in an orthopedic surgical procedure by providing both a locking mechanism that positively retains one or more fasteners thereto and a viewing window that results in an unobstructed view of the vertebrae and the bone graft.

Various aspects of this invention will become apparent to those skilled in the art from the following detailed description of the preferred embodiments, when read in light of the accompanying drawings.

BRIEF DESCRIPTION OF THE DRAWINGS

FIG. 5 is an exploded perspective view of a portion of a second plate and an actuator of the first embodiment of the cervical plate assembly illustrated in FIGS. 1 through 4.

FIG. 6 is an exploded perspective view of a portion of an alternative second plate and an alternative actuator that can be used with the first embodiment of the cervical plate assembly illustrated in FIGS. 1 through 4.

DETAILED DESCRIPTION OF THE PREFERRED EMBODIMENTS

Figure 1:
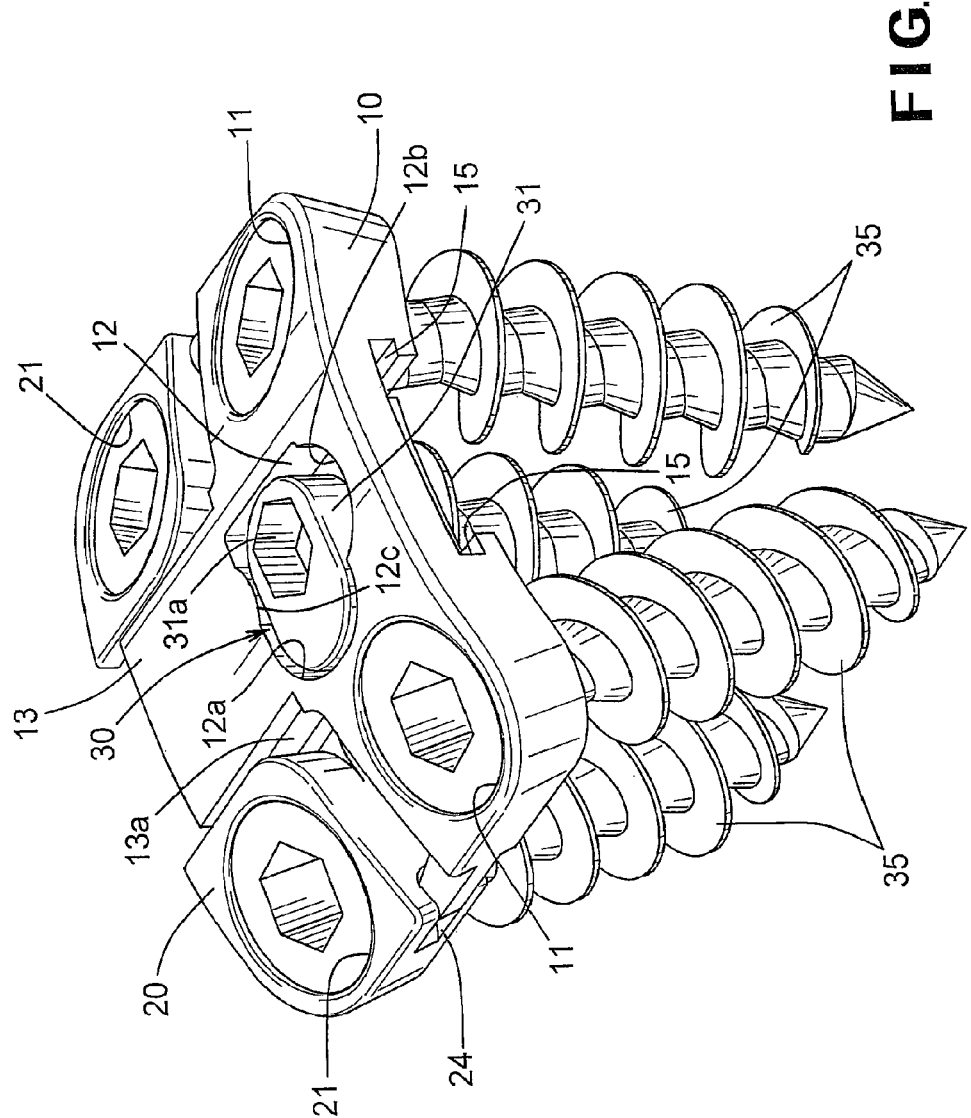
FIG. 1 is a perspective view from above of a first embodiment of a cervical plate assembly in accordance with this invention.

Referring now to the drawings, there is illustrated in FIGS. 1 through 9 a first embodiment of a cervical plate assembly in accordance with this invention. As will be explained in detail below, the first embodiment of the cervical plate assembly can be used to facilitate the fusion of two or more cervical vertebrae (not shown) by quickly and easily causing the vertebrae to exert a preloading force against a bone graft (not shown) that is interposed therebetween. However, the cervical plate assembly of this invention may be used for any desired purpose or in any desired surgical procedure, such as anterior lumbar spine surgery and other orthopedic applications, such as foot surgery.

The first embodiment of the cervical plate assembly includes a first plate 10 that can be formed from any desired (preferably rigid) material, such as titanium, stainless steel, cobalt-chrome, or other medically-approved biomaterial. The first plate 10 is generally flat and planar in shape and may, as illustrated, be gently curved from side to side and/or from end to end so as to conform to the natural curvature of the cervical spine. A pair of fastener openings 11 are formed through the first plate 10. In the illustrated embodiment, the fastener openings 11 are located on opposite sides of the first plate 10. However, the fastener openings 11 may be formed through the first plate 10 at any desired locations. Although two of such fastener openings 11 are shown in the illustrated embodiment, it will be appreciated that a greater or lesser number of such fastener openings 11 may be provided as desired. The purpose for the fastener openings 11 will be explained below.

The first plate 10 also includes an actuator opening 12 that is formed through the first plate 10. In the illustrated embodiment, the actuator opening 12 is located between the two fastener openings 11. However, the actuator opening 12 may be formed through the first plate 10 at any desired location. In the illustrated embodiment, the actuator opening 12 is shaped having a first lobe 12a and a second lobe 12b. The first lobe 12a is oriented generally parallel to a line extending between the two fastener openings 11, while the second lobe 12b is oriented generally perpendicular to such a line. Additionally, the illustrated actuator opening 12 includes an inwardly extending boss 12c that is generally aligned opposite from the second lobe 12b. However, the actuator opening 12 may be formed having any desired shape. The purpose for the actuator opening 12, the first and second lobes 12a and 12b, and the boss 12c will be explained below.

The first plate 10 further includes a guide portion 13 that, in the illustrated embodiment, is generally flat and planar in shape and may, as illustrated, be gently curved from side to side and/or from end to end. The illustrated guide portion 13 extends generally perpendicular to the line extending between the two fastener openings 11, although such is not required. The illustrated guide portion 13 also has a pair of flanges 13a provided on the lateral sides thereof, although such is not required. The purposes for the guide portion 13 and the lateral flanges 13a will be explained below.

The illustrated first plate 10 has a pair of alignment projections 14 that extend from the opposed sides thereof. The illustrated alignment projections 14 extend generally perpendicular to the line extending between the two fastener openings 11, although such is not required. The purpose for the alignment projections 14 will be explained below. Lastly, the illustrated first plate 10 has a pair of recesses 15 formed therein. In the illustrated embodiment, the recesses 15 are formed in the lower surface of the first plate 10 adjacent to the fastener openings 11 and extend generally perpendicular to the line extending between the two fastener openings 11, although such is not required. The purpose for the recesses 15 will be explained below.

The first embodiment of the cervical plate assembly also includes a second plate 20 that can be formed from any desired (preferably rigid) material, such as titanium, stainless steel, cobalt-chrome, or other medically-approved biomaterial. The second plate 20 is generally flat and planar in shape and may, as illustrated, be gently curved from side to side and/or from end to end. A pair of fastener openings 21 are formed through the second plate 20. In the illustrated embodiment, the fastener openings 21 are located on opposite sides of the second plate 20. However, the fastener openings 21 may be formed through the second plate 20 at any desired locations. Although two of such fastener openings 21 are shown in the illustrated embodiment, it will be appreciated that a greater or lesser number of such fastener openings 21 may be provided as desired. The purpose for the fastener openings 21 will be explained below.

The second plate 20 further includes a guide portion 22 that, in the illustrated embodiment, is generally flat and planar in shape and may, as illustrated, be gently curved from side to side and/or from end to end. The illustrated guide portion 22 extends generally perpendicular to the line extending between the two fastener openings 21, although such is not required. The illustrated guide portion 22 also has a pair of flanges 22a provided on the lateral sides thereof, although such is not required. The purposes for the guide portion 22 and the lateral flanges 22a will be explained below.

The second plate 20 also includes an actuator opening 23 that is formed through the second plate 20. In the illustrated embodiment, the actuator opening 23 is formed through the guide portion 22 of the second plate 20. However, the actuator opening 23 may be formed through the second plate 20 at any desired location. In the illustrated embodiment, the actuator opening 23 is generally circular in cross sectional shape. However, the actuator opening 23 may be formed having any desired shape. The purpose for the actuator opening 23 will be explained below.

The illustrated second plate 20 has a pair of alignment slots 24 that extend from the opposed sides thereof. The illustrated alignment slots 24 extend generally perpendicular to the line extending between the two fastener openings 21, although such is not required. The purpose for the alignment slots 24 will be explained below. Lastly, the illustrated second plate 20 has a pair of recesses 25 formed therein. In the illustrated embodiment, the recesses 25 are formed in the lower surface of the second plate 20 adjacent to the fastener openings 21 and extend generally perpendicular to the line extending between the two fastener openings 21, although such is not required. The purpose for the recesses 25 will be explained below.

The first embodiment of the cervical plate assembly further includes an actuator, indicated generally at 30, for selectively effecting movement of the first plate 10 and the second plate 20 relative to one another. In the illustrated embodiment, the actuator 30 includes an upper cam portion 31 and a lower journal portion 32. The illustrated upper cam portion 31 of the actuator 30 is generally oval in cross sectional shape. However, the upper cam portion 31 of the actuator 30 may be formed having any desired shape. When the first embodiment of the cervical plate assembly is assembled, the upper cam portion 31 of the actuator 30 is disposed within the actuator opening 12 formed through the first plate 10. The upper cam portion 31 has a drive mechanism 31a provided therein that is adapted to cooperate with a conventional tool (not shown) to effect rotation of the actuator 30 relative to the first and second plates 10 and 20. In the illustrated embodiment, the drive mechanism 31a is a hexagonally- shaped recess that can cooperate with a conventional hex key driver. However, the drive mechanism 31a can be embodied as any conventional structure for accomplishing this purpose.

The illustrated lower journal portion 32 of the actuator 30 is generally circular in cross sectional shape. However, the lower journal portion 32 of the actuator 30 may be formed having any desired shape. When the first embodiment of the cervical plate assembly is assembled, the lower journal portion 32 of the actuator 30 is disposed within the actuator opening 23 formed through the second plate 20. A retainer 33 is provided on the lower journal portion 32 of the actuator 30 to retain the actuator 30 with the first and second plates 10 and 20, as described below. The retainer 33 may be formed integrally with the lower journal portion 32 of the actuator 30, such as by deforming the bottom end of the lower journal portion 32 after assembly of the actuator 30. Alternatively, the retainer 33 may be formed as a separate piece that is secured to the lower journal portion 32 of the actuator 30 after installation within the actuator openings 12 and 23. The manner in which the actuator 30 selectively effects movement of the first plate 10 and the second plate 20 relative to one another will be explained below.

As discussed above and best shown in FIG. 5, the illustrated actuator opening 23 formed through the second plate 20 and the illustrated lower journal portion 32 of the actuator 30 are both generally circular in cross sectional shape. Preferably, the lower journal portion 32 of the actuator 30 is sized and shaped in accordance with the size and shape of the actuator opening 23 formed through the second plate 20. As a result, when the lower journal portion 32 of the actuator 30 is disposed within the actuator opening 23 formed through the second plate 20, the actuator 30 is journaled on the second plate 20 for free rotation relative thereto in either rotational direction.

Alternatively, the actuator 30 may be journaled on the second plate 20 for free rotation relative thereto in only a single rotational direction. FIG. 6 illustrates a portion of an alternative second plate 20' and an alternative actuator 30' that can be used with the first embodiment of the cervical plate assembly illustrated in FIGS. 1 through 5 to accomplish this. The alternative second plate 20' and actuator 30' are similar to the second plate 20 and actuator 30 described above, and like reference numbers are used to indicate similar parts. In this alternative embodiment, however, the actuator opening 23' formed through the second plate 20' has an extended portion 23a' that defines an arm therebetween. One or more ratchet teeth 23b' are provided on the flexible arm facing inwardly toward the lower journal portion 32' of the actuator 30'. Similarly, the lower journal portion 32' of the actuator 30' has one or more ratchet teeth 32a' thereon facing outwardly toward the arm. The ratchet teeth 23b' and 32a' cooperate in a conventional manner to permit the actuator 30' to rotate freely relative to the second plate 20' in a first rotational direction, but prevent such free relative rotation in a second rotational direction that is opposite to the first rotational direction. The purpose for providing the ratchet teeth 23b' and 32a' will be explained below.

Lastly, one or more fasteners 35 are provided to secure the first embodiment of the cervical plate assembly to one or more bones in a human body, such as a pair of vertebrae in a spine. The fasteners 35 are conventional in the art and may be embodied as bone screws or other known threaded fasteners. The fasteners 35 are adapted to extend through the fastener openings 11 and 21 respectively formed through the first and second plates 10 and 20. The manner in which the fasteners 35 are used will be explained below.

Figure 2:
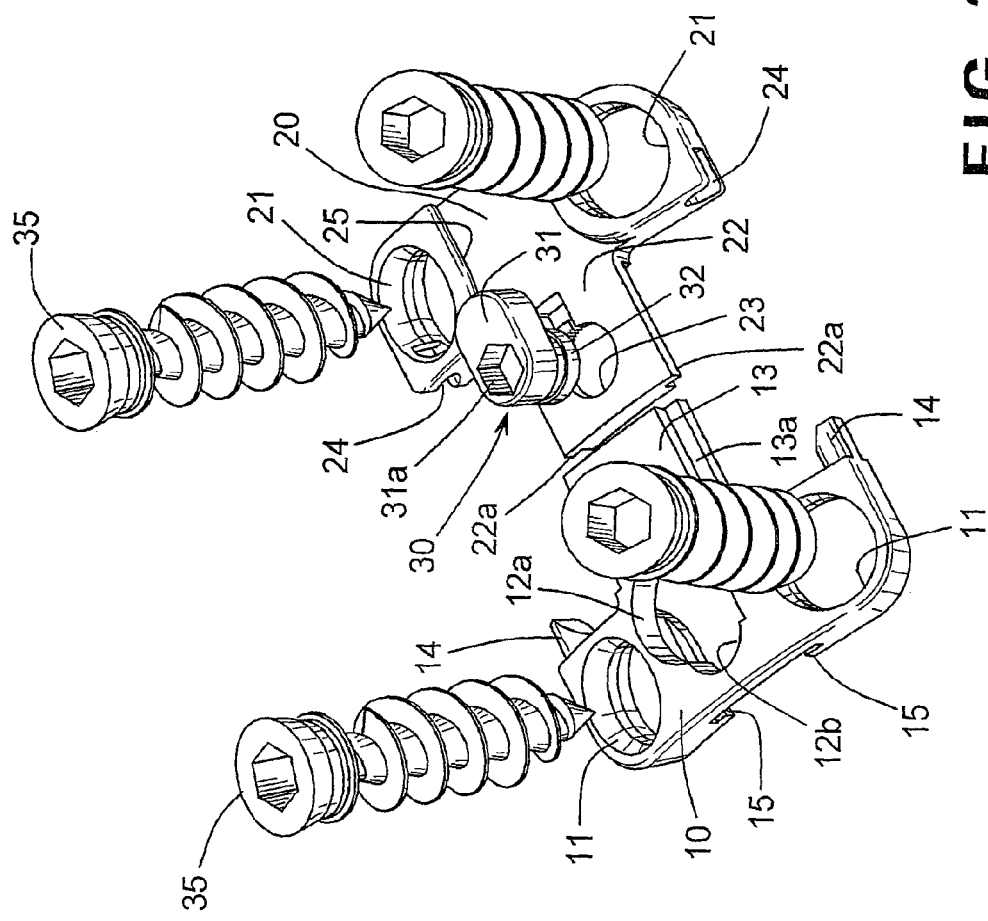
FIG. 2 is an exploded perspective view of the first embodiment of the cervical plate assembly illustrated in FIG. 1.
Figure 3:
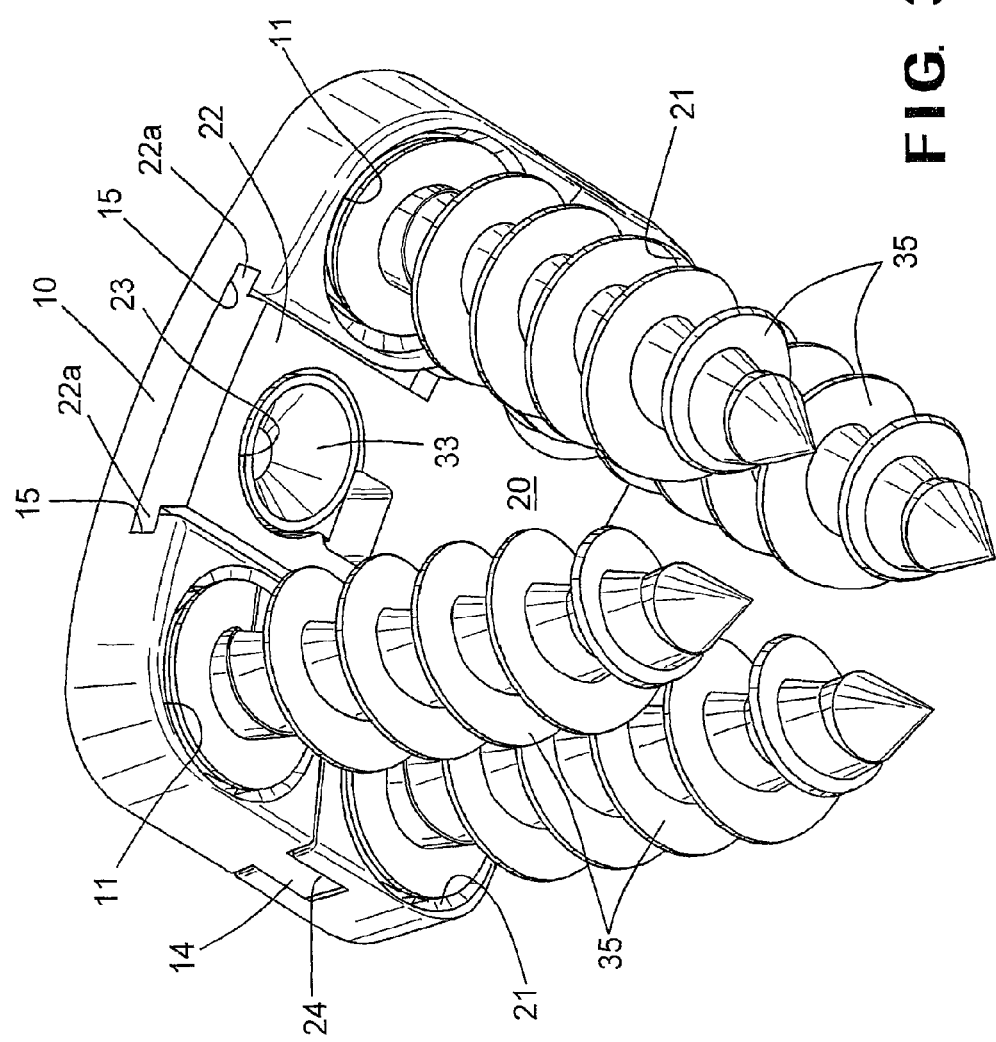
FIG. 3 is a perspective view from below of the first embodiment of the cervical plate assembly illustrated in FIGS. 1 and 2.
Figure 4:
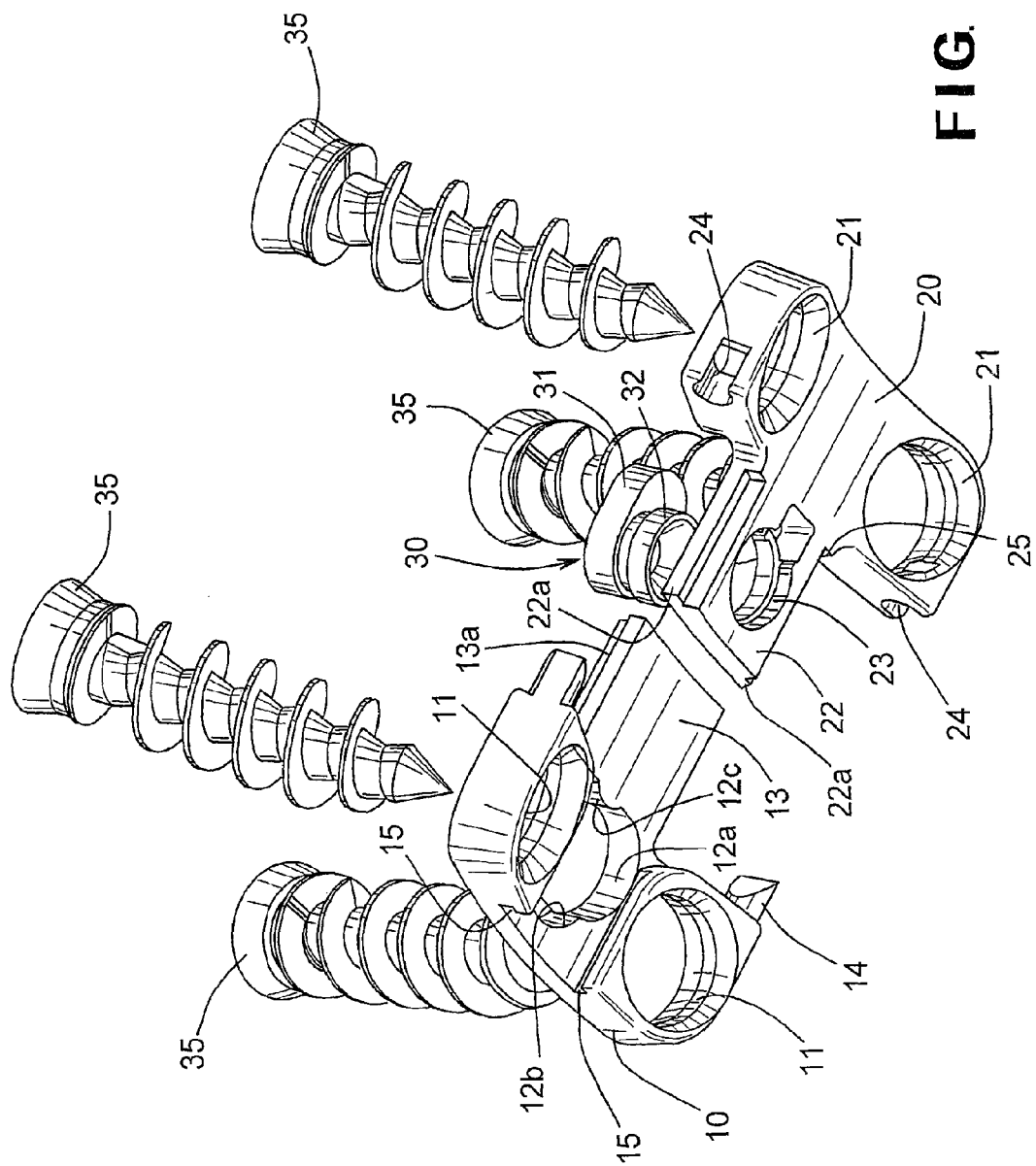
FIG. 4 is an exploded perspective view of the first embodiment of the cervical plate assembly illustrated in FIG. 3.

The first embodiment of the cervical plate assembly can be assembled by initially orienting the first and second plates 10 and 20 as shown in FIG. 2, wherein the respective guide portions 13 and 22 face one another. The first and second plates 10 and 20 are then moved toward one another such that the guide portion 13 provided on the first plate 10 is disposed over the guide portion 22 provided on the second plate 20, and the respective actuator openings 12 and 23 are aligned with one another. During this movement, the flanges 13a provided on the lateral sides of the guide portion 13 are received within the recesses 25 provided in the second plate 20, and the flanges 22a provided on the lateral sides of the guide portion 22 are received within the recesses 15 provided in the first plate 10. Similarly, the alignment projections 14 provided on the first plate 10 are received within the alignment slots 24 provided in the second plate 20. Thus, when assembled, the first and second plates 10 and 20 engage one another for sliding movement toward and away from one another, but are positively restrained from any other relative movement.

While the actuator openings 12 and 23 are aligned with one another, the actuator 30 is next inserted therein such that the upper cam portion 31 of the actuator 30 is disposed within the actuator opening 12 formed through the first plate 10 and the lower journal portion 32 of the actuator 30 is journaled within the actuator opening 23 formed through the second plate 20. Following such insertion, the retainer 33 is secured to the lower journal portion 32 of the actuator 30 to retain the actuator 30 with the first and second plates 10 and 20.

Figure 7:
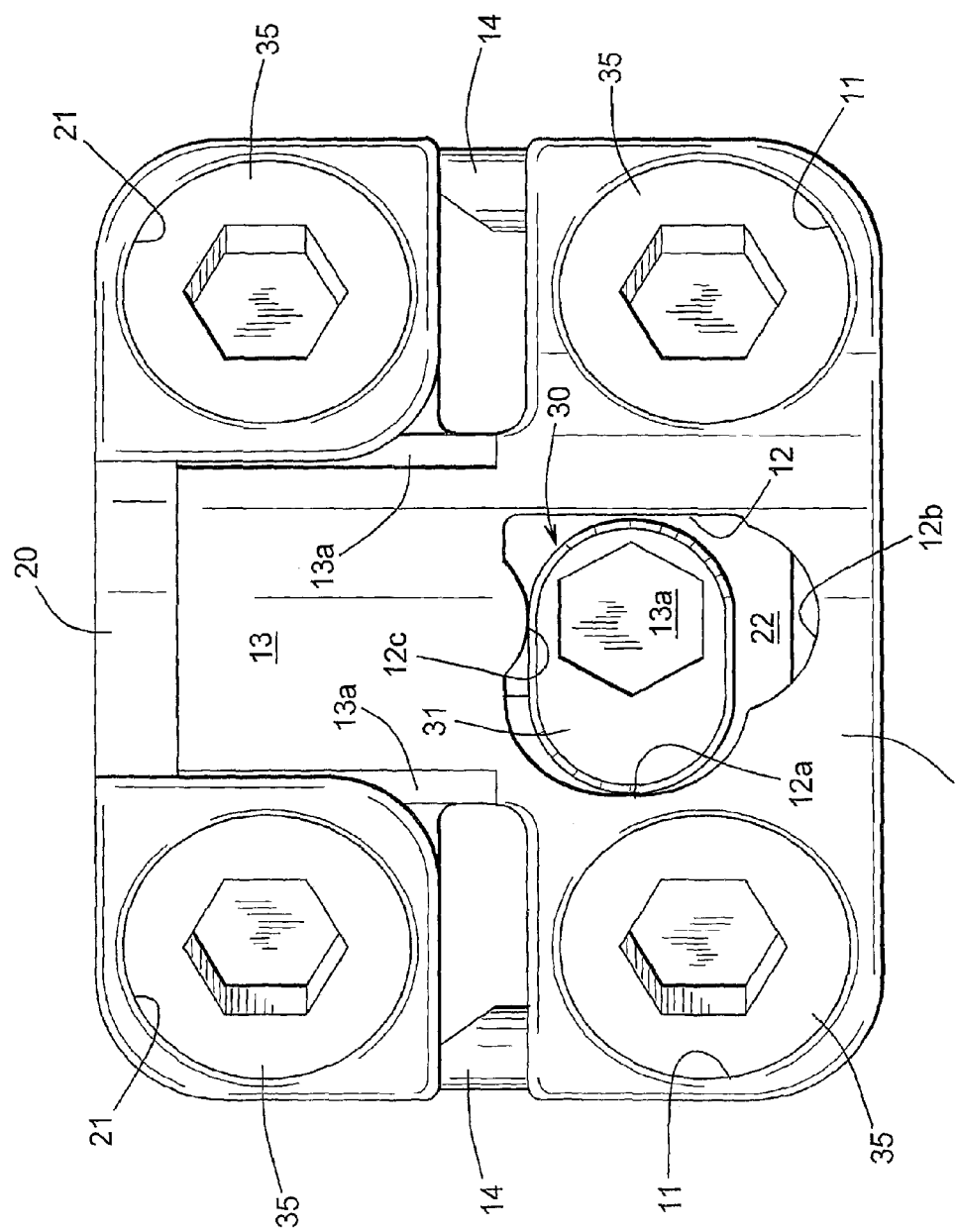
FIG. 7 is a top plan view of the first embodiment of the cervical plate assembly illustrated in FIGS. 1 through 5 shown in an initial uncompressed orientation.
Figure 8:
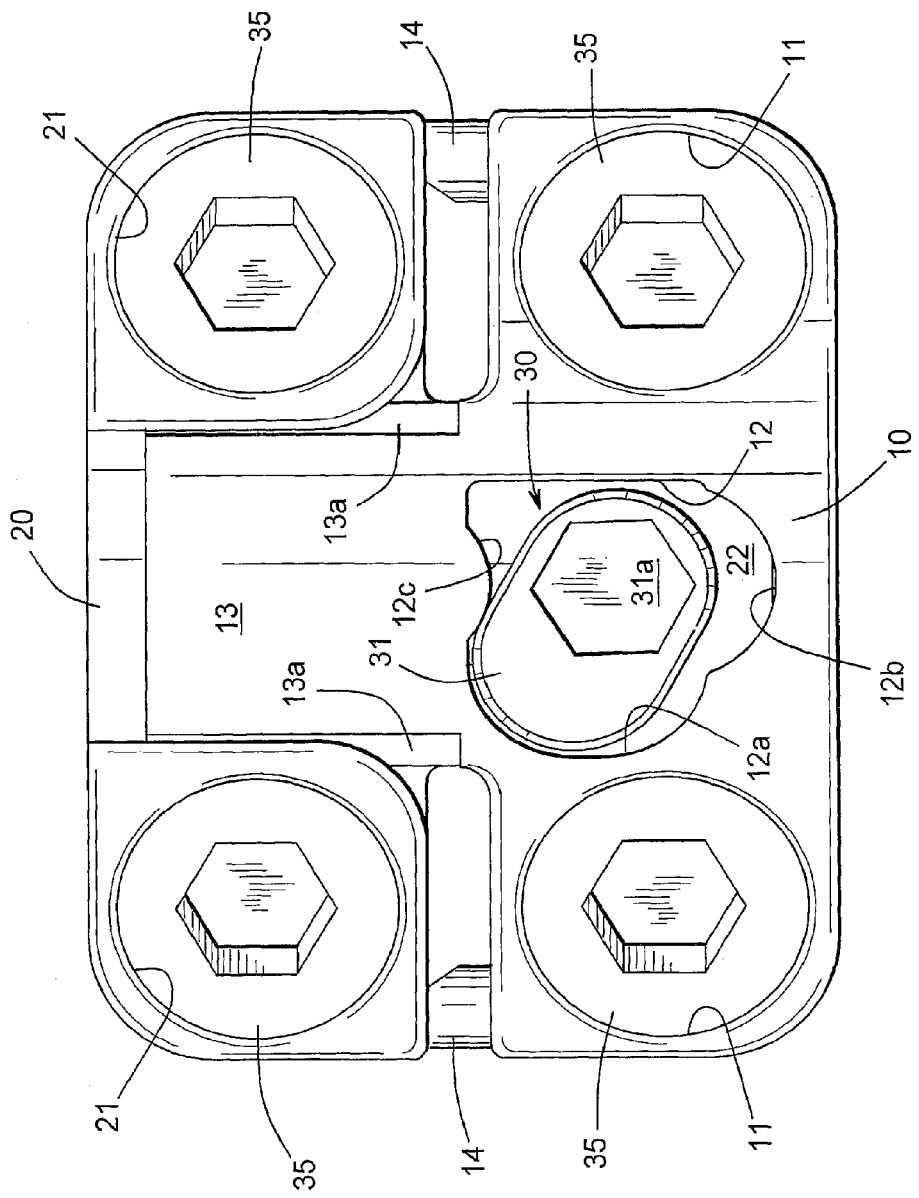
FIG. 8 is a top plan view similar to FIG. 7 showing the first embodiment of the cervical plate assembly in an intermediate orientation.
Figure 9:
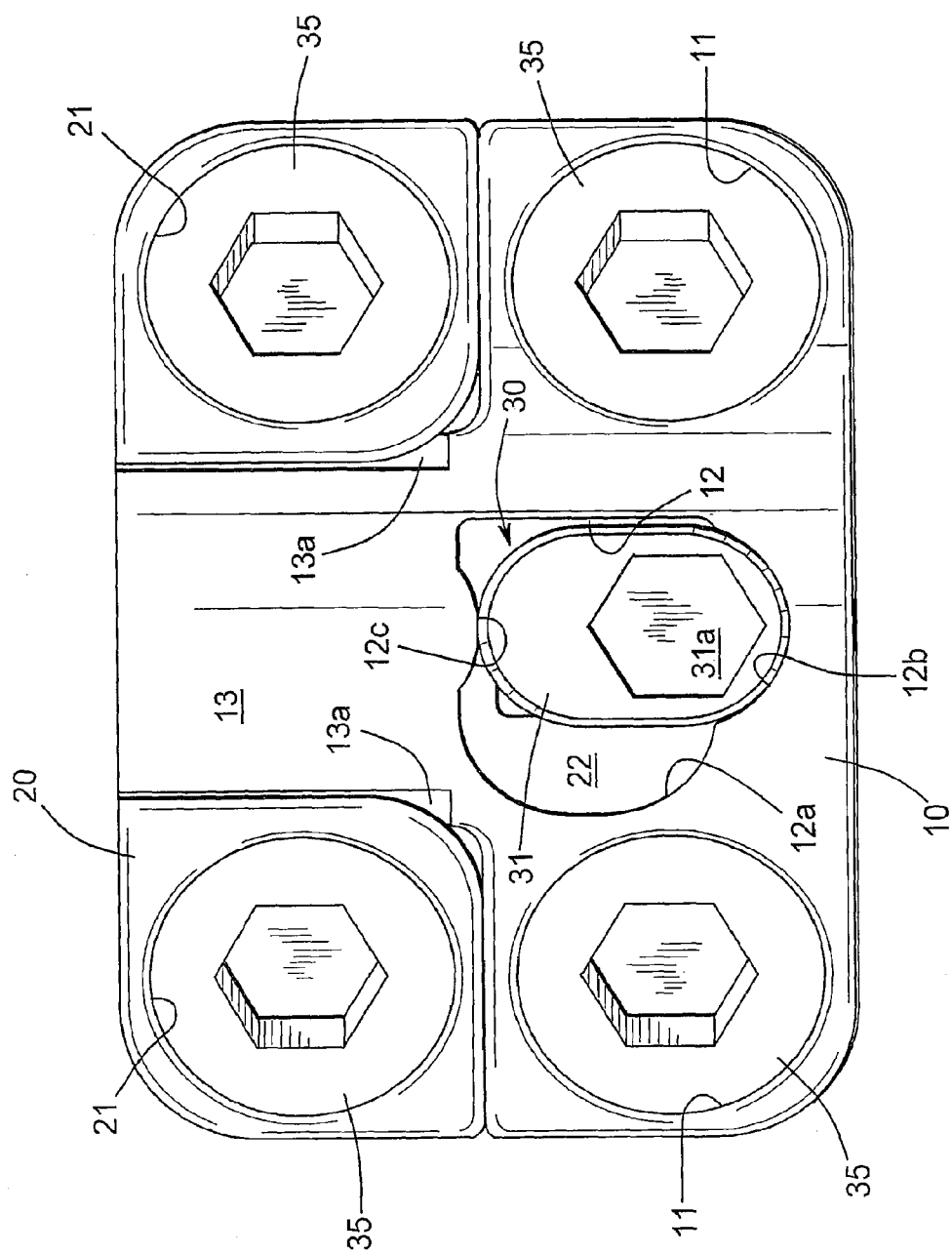
FIG. 9 is a top plan view similar to FIG. 8 showing the first embodiment of the cervical plate assembly in a final compressed orientation.

As mentioned above, the actuator 30 is provided to selectively effect sliding movement of the first plate 10 and the second plate 20 relative to one another. The manner in which this is accomplished is best illustrated in FIGS. 7, 8, and 9. FIG. 7 illustrates the first and second plates first embodiment of the cervical plate assembly illustrated in FIGS. 1 through 5 shown in an initial uncompressed orientation, wherein the fastener openings 11 and 21 of the first and second plates 10 and 20, respectively, are spaced apart from one another by a relatively large distance. In this initial uncompressed orientation, the upper cam portion 31 of the actuator 30 is aligned with the first lobe 12a of the actuator opening 12 formed through the first plate 10 (i.e., generally parallel to a line extending between the two fastener openings 11).

In order to move the first and second plates 10 and 20 from the initial uncompressed orientation illustrated in FIG. 7 through the intermediate orientation illustrated in FIG. 8 to the final compressed orientation illustrated in FIG. 9, the actuator 30 is rotated relative to such plates 10 and 20, such as by using the conventional hex key driver mentioned above. In the views shown in FIGS. 7, 8, and 9, the actuator 30 is rotated clockwise rotated relative to such plates 10 and 20. As a result, the upper cam portion 31 of the actuator 30 is moved out of alignment with the first lobe 12a and into alignment with the second lobe 12b of the actuator opening 12 formed through the first plate 10 (i.e., generally perpendicular to a line extending between the two fastener openings 11). During such rotation, the upper cam portion 31 of the actuator 30 abuts portions of the inner surface of the actuator opening 12, causing the first and second plates 10 and 20 to slide relative to one another. This is because the upper cam portion 31 of the illustrated actuator 30 is eccentric with the lower cam portion 32 thereof. As such rotation of the actuator 30 continues, the first and second plates 10 and 20 continue to slide toward one another through the intermediate orientation illustrated in FIG. 8 to the final compressed orientation illustrated in FIG. 9, wherein the fastener openings 11 and 21 of the first and second plates 10 and 20, respectively, are spaced apart from one another by a relatively small distance.

If desired, when the first and second plates 10 and 20 are oriented in the final compressed orientation illustrated in FIG. 9, the upper cam portion 31 of the actuator 30 may be slightly compressed between the inwardly extending boss 12c provided on the actuator opening 12 and the opposed portion of the second lobe 12b. The friction generated by such compression of the upper cam portion 31 of the actuator 30 functions to positively retain the first and second plates 10 and 20 in this final compressed orientation and prevent any inadvertent sliding of the first and second plates 10 and 20 back toward the intermediate orientation illustrated in FIG. 8. Alternatively, the ratchet teeth 23b' and 32a' respectively provided on the alternative second plate 20' and the alternative actuator 30' illustrated in FIG. 6 can be used to positively retain the first and second plates 10 and 20 in this final compressed orientation or, alternatively, at any intermediate orientation between the initial uncompressed and final compressed orientations.

Figure 10:
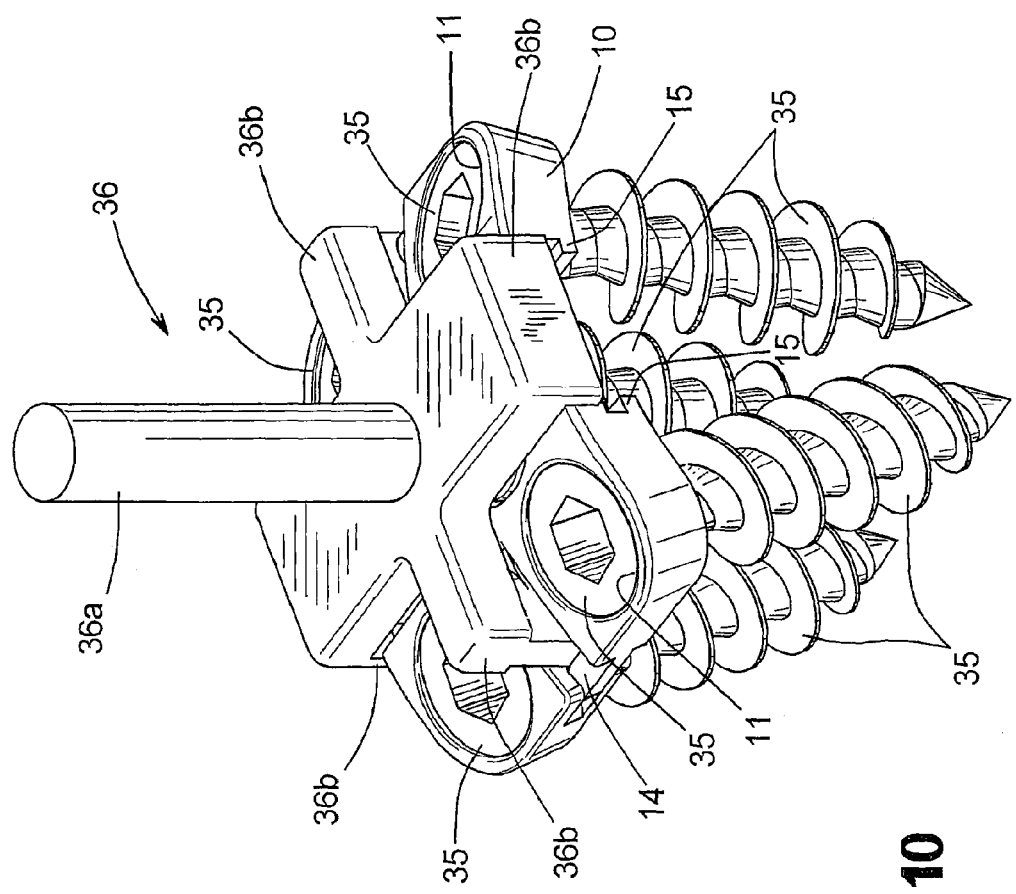
FIG. 10 is a perspective view showing an installation tool installed on the first embodiment of the cervical plate assembly illustrated in FIGS. 1 through 9 to positively maintain the first and second plates in the initial uncompressed orientation.
Figure 11:
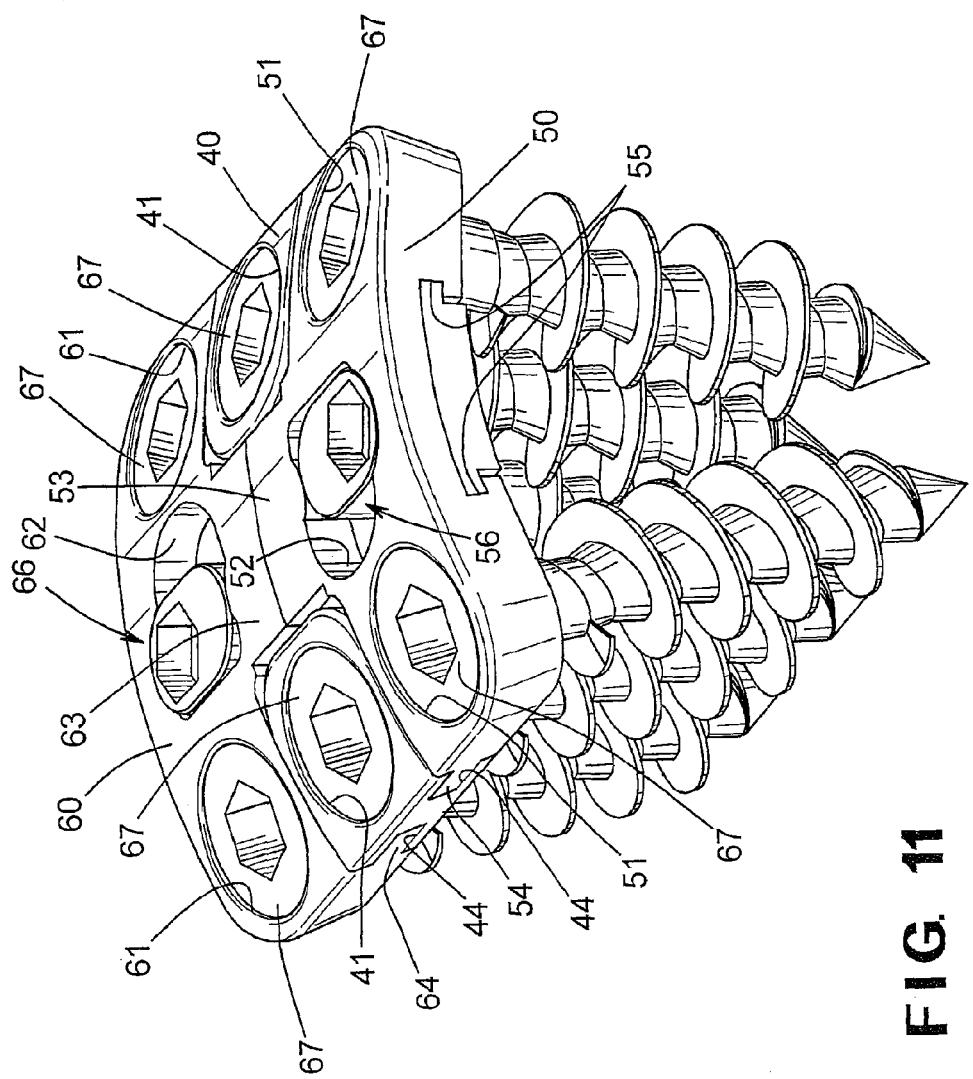
FIG. 11 is a perspective view from above of a second embodiment of a cervical plate assembly in accordance with this invention.
Figure 12:
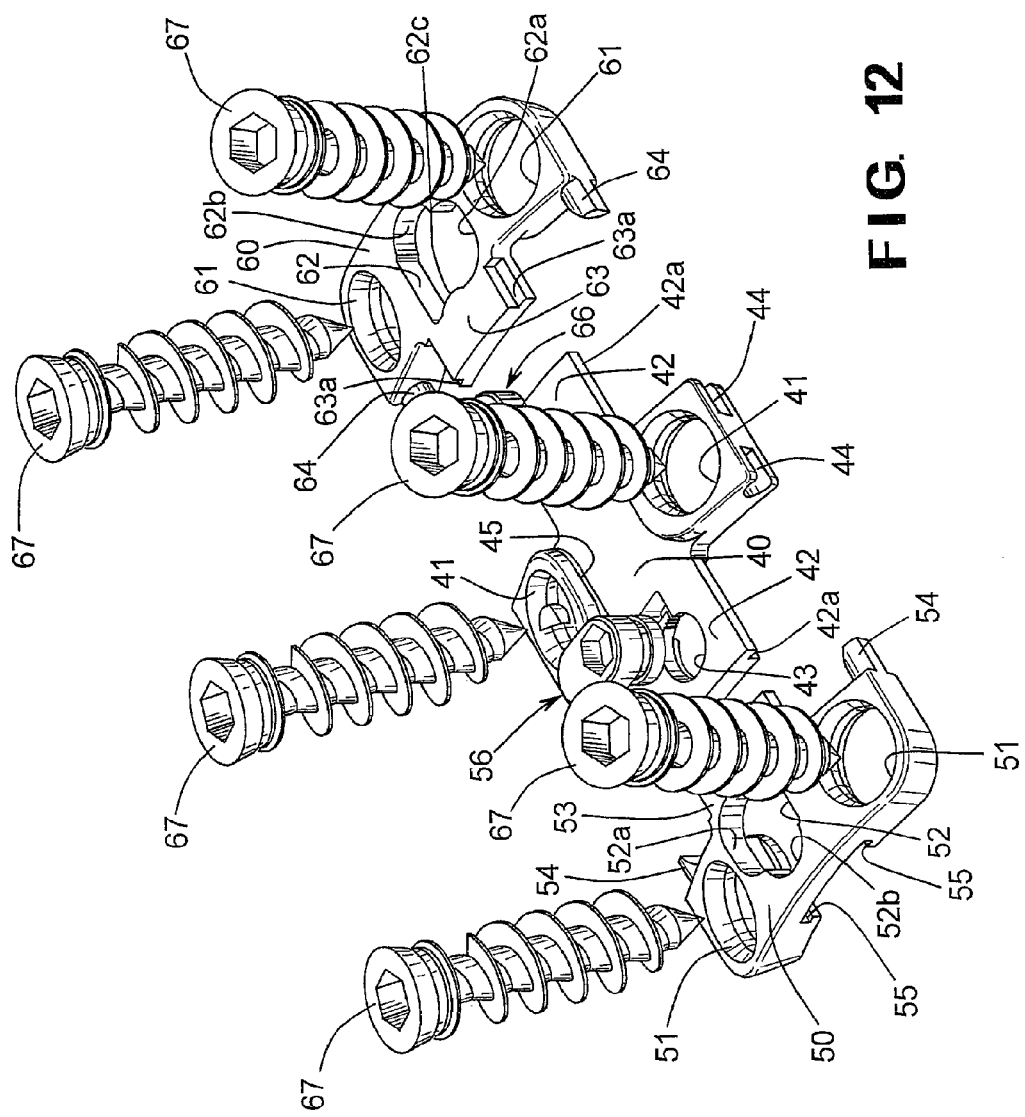
FIG. 12 is an exploded perspective view of the second embodiment of the cervical plate assembly illustrated in FIG. 11.

In practice, the first embodiment of the cervical plate assembly of this invention can be used to facilitate the performance of a cervical spinal fusion procedure. As described above, such a cervical spinal fusion procedure typically involves the insertion of a bone graft in the space between the vertebrae. After the bone graft has been inserted between the vertebrae, the first embodiment of the cervical plate assembly can be used to fix the spacing and alignment of such vertebrae relative to one another to allow the fusion process to occur. To accomplish this, the first and second plates 10 and 20 are moved to the initial uncompressed orientation illustrated in FIG. 7, wherein the fastener openings 11 and 21 of the first and second plates 10 and 20, respectively, are spaced apart from one another by a relatively large distance. If desired, an installation tool, such as indicated generally at 36 in FIG. 10, can be used to positively maintain the first and second plates 10 and 20 in the initial uncompressed orientation. The illustrated installation tool 36 include a handle 36a having a plurality of arms 36b depending therefrom. The arms 36b can be sized and shaped to fit snugly between adjacent portions of the first and second plates 10 and 20 and thereby positively maintain such plates 10 and 20 in the initial uncompressed orientation.

Regardless of whether the installation tool 36 is used, the first embodiment of the cervical plate assembly is next secured to the desired vertebrae. This can be accomplished by securing the first plate 10 to a first vertebra using the fasteners 35, which can be inserted through the fastener openings 11 into engagement with the vertebra in any desired manner. Similarly, the second plate 20 can be secured to a second vertebra by means of the fasteners 35, which can be inserted through the fastener openings 21 into engagement with the vertebra in any desired manner.

After the first and second plates 10 and 20 have been secured to the respective vertebrae, the actuator 30 is used to move such plates 10 and 20 from the initial uncompressed orientation illustrated in FIG. 7 through the intermediate orientation illustrated in FIG. 8 to the final compressed orientation illustrated in FIG. 9 as described above. Alternatively, as mentioned above, the plates 10 and 20 can be moved from the initial uncompressed orientation illustrated in FIG. 7 and maintained in any desired intermediate position by means of the ratchet teeth 23b' and 32a' respectively provided on the alternative second plate 20' and the alternative actuator 30'. In either event, the fastener openings 11 and 21 (along with the associated fasteners 35 and the vertebrae to which the fasteners 35 are secured) are moved closer together. This causes the vertebrae to engage and compress the bone graft that is disposed therebetween, thereby facilitation the fusion of the vertebrae as described above. The first embodiment of the cervical plate assembly can remain secured to these vertebrae until such fusion has occurred, at which time it can be removed I a subsequent surgical procedure.

Referring now to FIGS. 11 through 15, a second embodiment of a cervical plate assembly in accordance with this invention is illustrated. The second embodiment of the cervical plate assembly can be used facilitate to the fusion of three or more cervical vertebrae by quickly and easily causing the vertebrae to exert a preloading force against bone grafts (not shown) that are interposed therebetween. However, the cervical plate assembly of this invention may be used for any desired purpose or in any desired surgical procedure.

The second embodiment of the cervical plate assembly includes a center plate 40 that can be formed from any desired (preferably rigid) material, such as titanium, stainless steel, cobalt-chrome, or other medically-approved biomaterial. The center plate 40 is generally flat and planar in shape and may, as illustrated, be gently curved from side to side and/or from end to end. A pair of fastener openings 41 are formed through the center plate 40. In the illustrated embodiment, the fastener openings 41 are located on opposite sides of the second plate 40. However, the fastener openings 41 may be formed through the second plate 40 at any desired locations. Although two of such fastener openings 41 are shown in the illustrated embodiment, it will be appreciated that a greater or lesser number of such fastener openings 41 may be provided as desired. The purpose for the fastener openings 41 will be explained below.

The center plate 40 further includes first and second guide portions 42 that, in the illustrated embodiment, are generally flat and planar in shape and may, as illustrated, be gently curved from side to side and/or from end to end. The illustrated guide portions 42 extend generally perpendicular to the line extending between the two fastener openings 41, although such is not required. The illustrated guide portions 42 also have respective pairs of flanges 42a provided on the lateral sides thereof, although such is not required. The purposes for the guide portions 42 and the lateral flanges 42a will be explained below.

The center plate 40 also includes a pair of actuator openings 43 that are formed through the center plate 40. In the illustrated embodiment, the actuator openings 43 are formed through the guide portions 42 of the center plate 40. However, the actuator openings 43 may be formed through the center plate 40 at any desired locations. In the illustrated embodiment, the actuator openings 43 are generally circular in cross sectional shape. However, the actuator openings 43 may be formed having any desired shapes. The purpose for the actuator openings 43 will be explained below.

The illustrated center plate 40 has first and second pairs of alignment slots 44 (only one pair is illustrated) that extend from the opposed sides thereof. The illustrated alignment slots 44 extend generally perpendicular to the line extending between the two fastener openings 44, although such is not required. The purpose for the alignment slots 44 will be explained below. Lastly, the illustrated center plate 40 has first and second pairs of recesses 45 formed therein. In the illustrated embodiment, the recesses 45 are formed in the lower surface of the center plate 40 adjacent to the fastener openings 21 and extend generally perpendicular to the line extending between the two fastener openings 41, although such is not required. The purpose for the recesses 45 will be explained below.

The second embodiment of the cervical plate assembly also includes a first side plate 50 that is similar in structure and operation to the first plate 10 described above. The first side plate 50 includes a pair of fastener openings 51, an actuator opening 52 having a first lobe 52a and a second lobe 52b, a guide portion 53 having a pair of flanges 53a provided on the lateral sides thereof, a pair of alignment projections 54 that extend from the opposed sides thereof, and a pair of recesses 55 formed therein. A first actuator, indicated generally at 56, is provided for selectively effecting movement of the center plate 40 and the first side plate 50 relative to one another. The structure and manner of operation of the first actuator 56 can be the same as described above in connection with the actuator 30.

The second embodiment of the cervical plate assembly further includes a second side plate 60 that is also similar in structure and operation to the first plate 10 described above. The second side plate 60 includes a pair of fastener openings 61, an actuator opening 62 having a first lobe 62a and a second lobe 62b, a guide portion 63 having a pair of flanges 63a provided on the lateral sides thereof, a pair of alignment projections 64 that extend from the opposed sides thereof, and a pair of recesses 65 formed therein. A second actuator, indicated generally at 66, is provided for selectively effecting movement of the center plate 40 and the second side plate 60 relative to one another. The structure and manner of operation of the second actuator 66 can also be the same as described above as described above in connection with the actuator 30.

Conventional fasteners 67 (similar to the fasteners 35 described above) can be used to secure the second embodiment of the cervical plate assembly to a plurality of vertebrae (not shown) in the manner described above. In the illustrated embodiment, a first pair of the fasteners 67 extend through the respective fastener openings 41 formed through the center plate 40 into engagement with a first vertebra. Also, a second pair of the fasteners 67 extend through the respective fastener openings 51 formed through the first side plate 50 into engagement with a second vertebra. Lastly, a third pair of the fasteners 67 extend through the respective fastener openings 61 formed through the second side plate 60 into engagement with a third vertebra.

Figure 13:
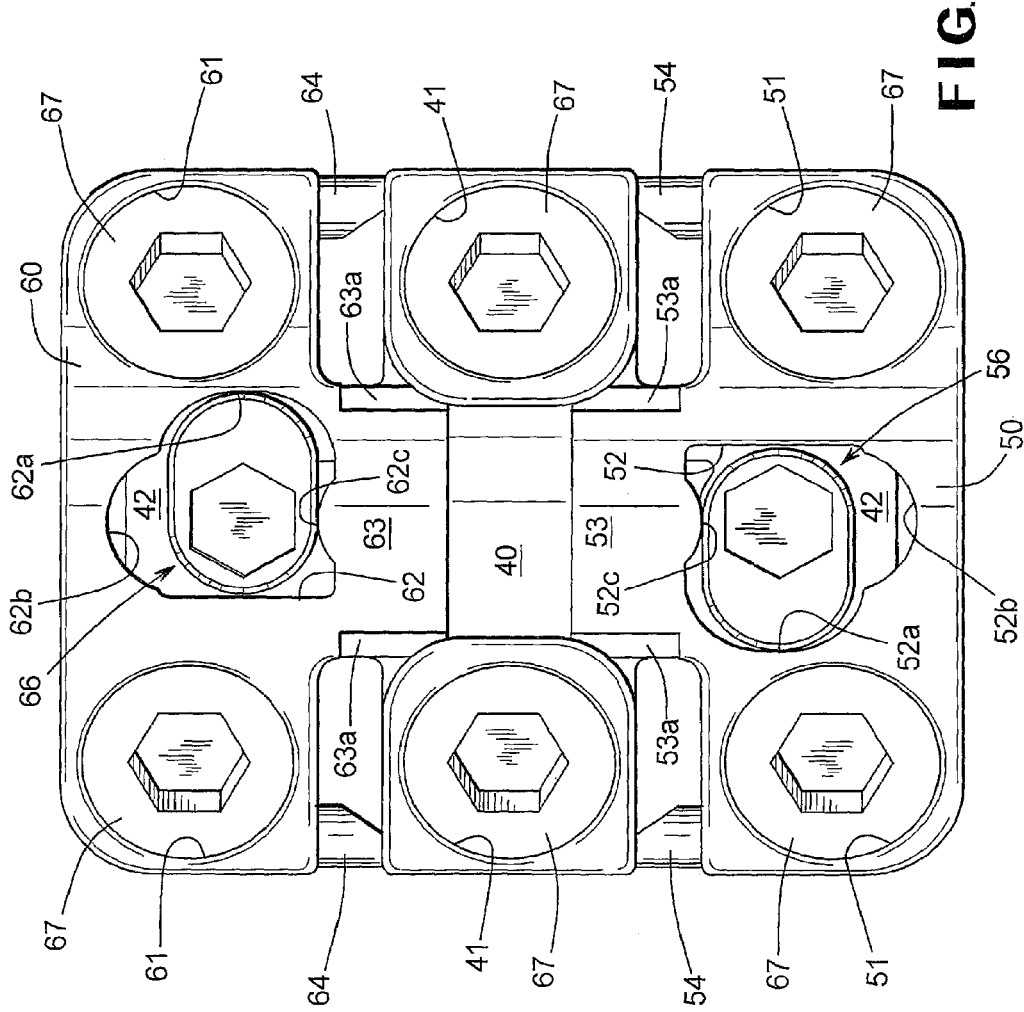
FIG. 13 is a top plan view of the second embodiment of the cervical plate assembly illustrated in FIGS. 11 and 12 shown in an initial uncompressed orientation.
Figure 14:
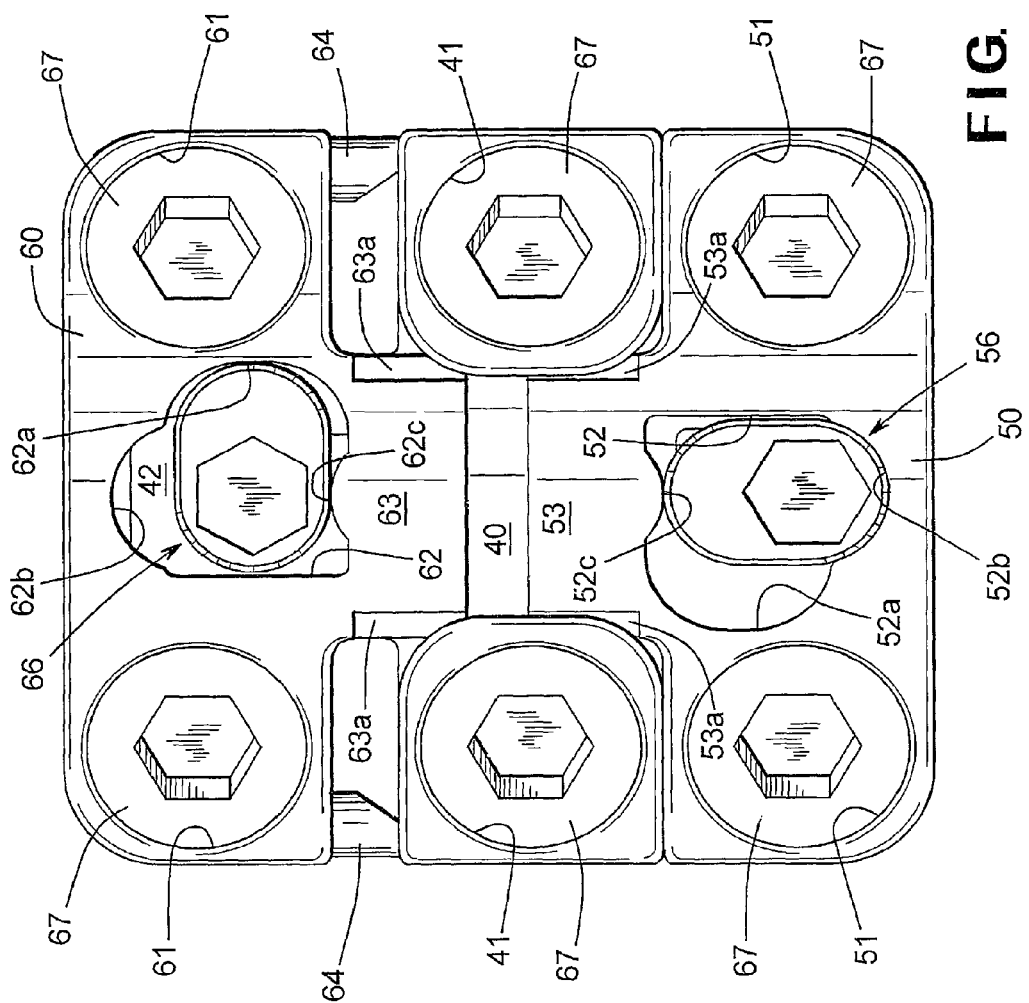
FIG. 14 is a top plan view similar to FIG. 13 showing the second embodiment of the cervical plate assembly in an intermediate orientation.
Figure 15:
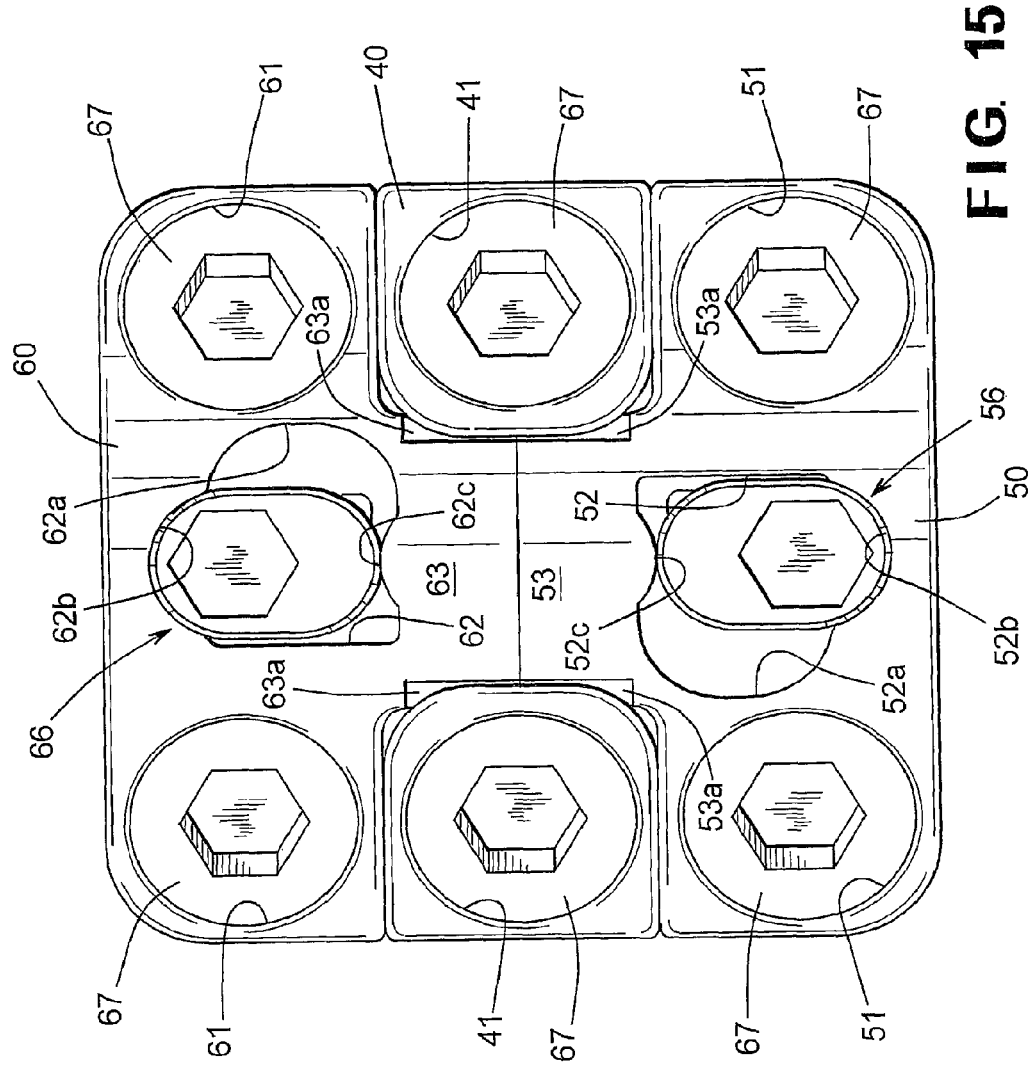
FIG. 15 is a top plan view similar to FIG. 14 showing the second embodiment of the cervical plate assembly in a final compressed orientation.

FIGS. 13, 14, and 15 illustrate the operation of the second embodiment of the cervical plate assembly of this invention. In FIG. 13, each of the first and second side plates 50 and 60 is shown in an initial uncompressed orientation relative to the center plate 40. In order to move the first side plate 50 from the initial uncompressed orientation illustrated in FIG. 13 through an intermediate orientation to a final compressed orientation illustrated in FIG. 14, the first actuator 56 is rotated relative to such plates 40 and 50. As a result, the upper cam portion of the first actuator 56 is moved out of alignment with the first lobe 52a and into alignment with the second lobe 52b of the actuator opening 52 formed through the first side plate 50. As such rotation of the first actuator 56 continues, the plates 40 and 50 slide toward one another through the intermediate orientation to the final compressed orientation illustrated in FIG. 14, wherein the fastener openings 41 and 51 of the plates 40 and 50, respectively, are spaced apart from one another by a relatively small distance.

Similarly, in order to move the second side plate 60 from the initial uncompressed orientation illustrated in FIG. 13 through an intermediate orientation to a final compressed orientation illustrated in FIG. 15, the second actuator 67 is rotated relative to such plates 40 and 60. As a result, the upper cam portion of the second actuator 66 is moved out of alignment with the first lobe 62a and into alignment with the second lobe 62b of the actuator opening 62 formed through the second side plate 60. As such rotation of the second actuator 67 continues, the plates 40 and 60 slide toward one another through the intermediate orientation to the final compressed orientation illustrated in FIG. 15, wherein the fastener openings 41 and 61 of the plates 40 and 60, respectively, are spaced apart from one another by a relatively small distance.

Figure 16:
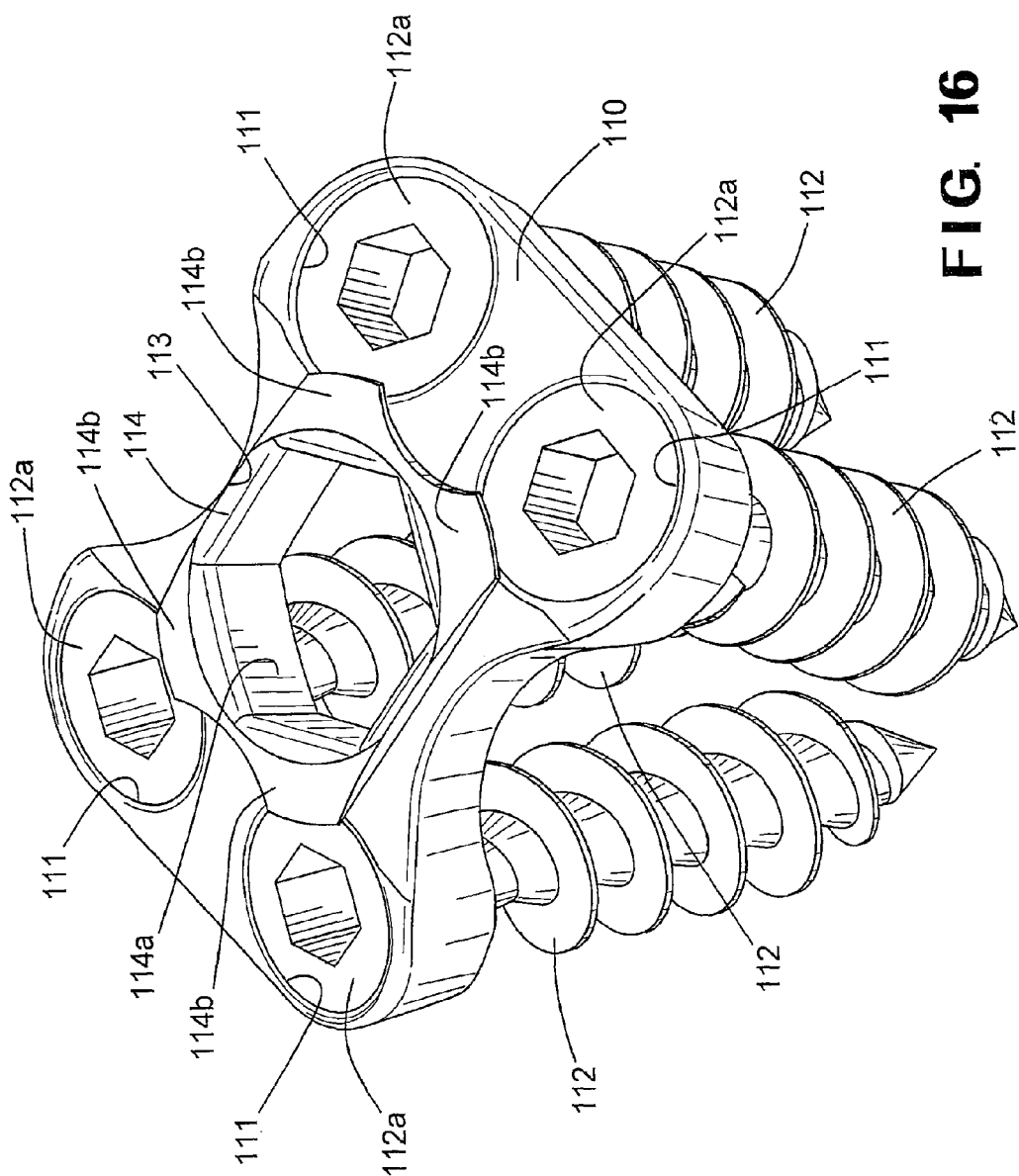
FIG. 16 is a perspective view of a third embodiment of a cervical plate assembly in accordance with this invention, wherein a locking member is shown in a locked position.
Figure 17:
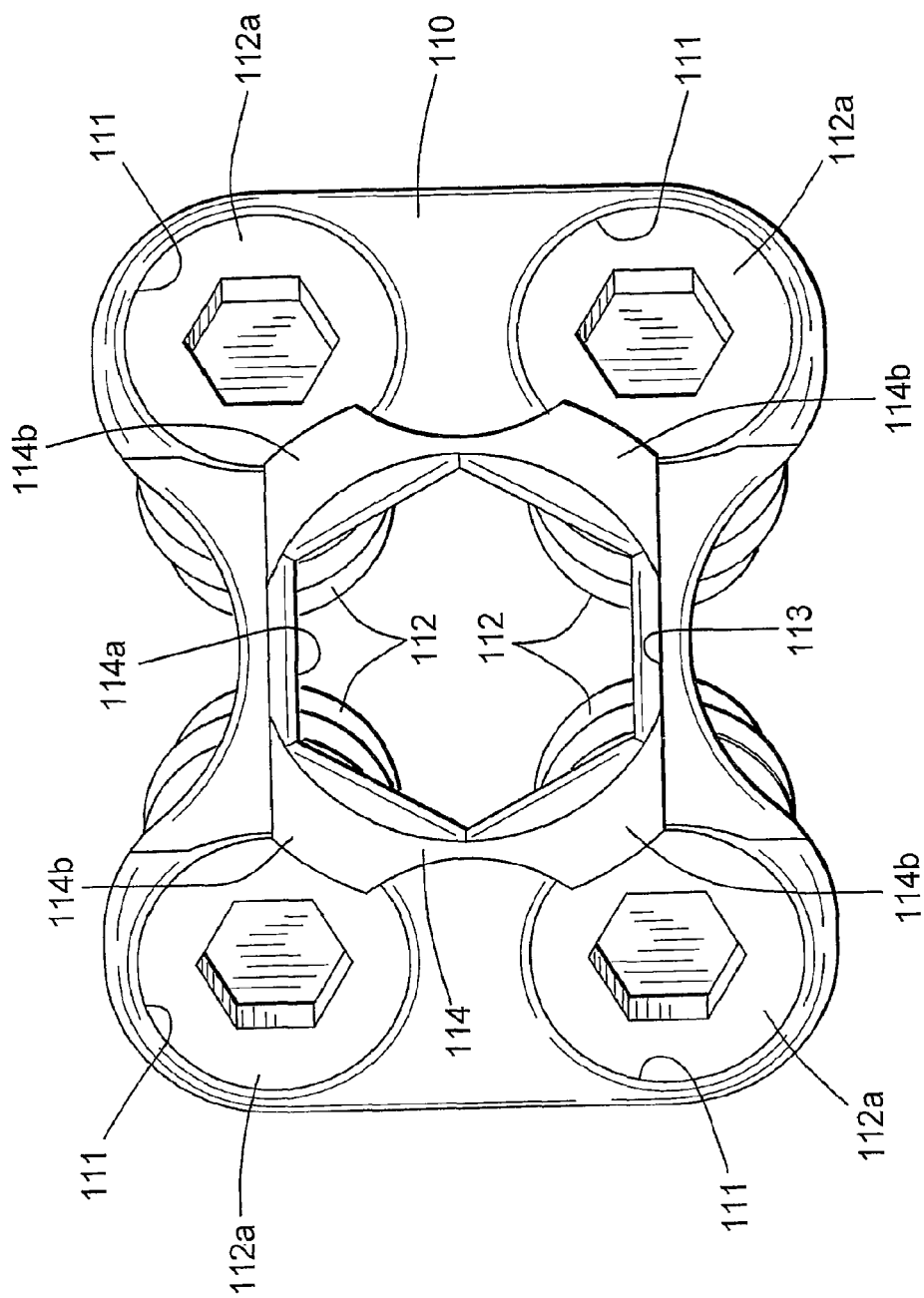
FIG. 17 is a top plan view of the third embodiment of the cervical plate assembly illustrated in FIG. 16 wherein the locking member is shown in the locked position.
Figure 18:
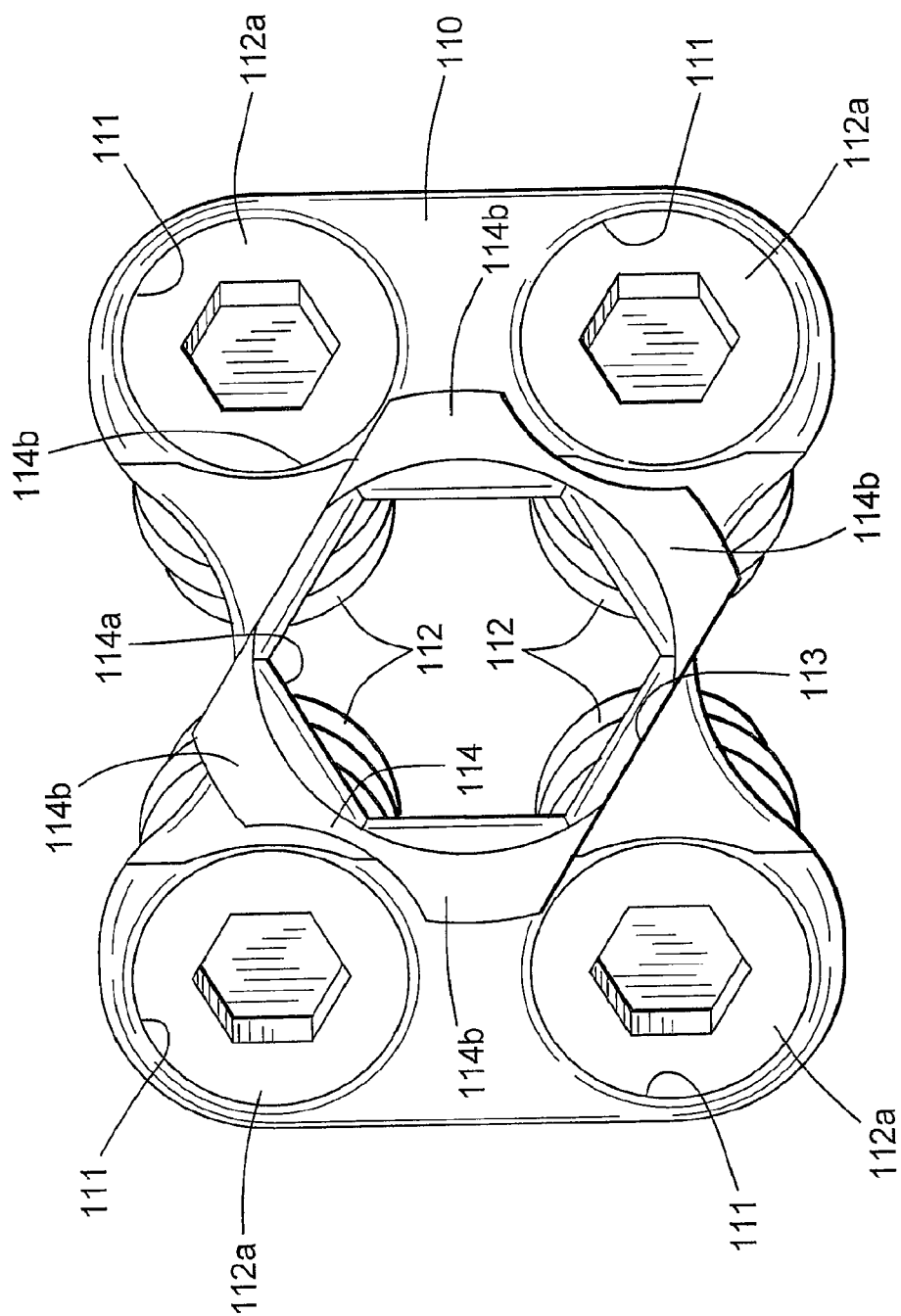
FIG. 18 is a top plan view of the third embodiment of the cervical plate assembly illustrated in FIGS. 16 and 17 wherein the locking member is shown in an unlocked position.

Referring now to FIGS. 16 through 18, a third embodiment of a cervical plate assembly in accordance with this invention is illustrated. The third embodiment of the cervical plate assembly can be used facilitate to the fusion of two or more cervical vertebrae without, however, causing the vertebrae to exert a preloading force against bone grafts (not shown) that are interposed therebetween, as described above. However, the third embodiment of the cervical plate assembly provides both a locking mechanism that positively retains one or more fasteners thereto and a viewing window that results in an unobstructed view of the vertebral edges and the interposed bone graft.

The third embodiment of the cervical plate assembly includes a plate 110 that can be formed from any desired (preferably rigid) material, such as titanium, stainless steel, cobalt-chrome, or other medically-approved biomaterial. The plate 110 is generally flat and planar in shape and may, as illustrated, be gently curved from side to side and/or from end to end. First and second pairs of fastener openings 111 are formed through the plate 110. In the illustrated embodiment, the fastener openings 111 are located on the opposite sides of the plate 110. However, the fastener openings 111 may be formed through the plate 110 at any desired locations. Although two pairs of such fastener openings 111 are shown in the illustrated embodiment, it will be appreciated that a greater or lesser number of such fastener openings 111 may be provided as desired. Respective fasteners 112 are provided within each of the fastener openings 111 to secure the third embodiment of the cervical plate assembly to one or more bones in a human body, such as a pair of vertebrae in a spine, in the manner described above. Each of the fasteners 112 includes an outer end surface 112a.

An opening 113 is formed through the plate 110. In the illustrated embodiment, the opening 113 is generally circular in shape and is located at the center of the plate 110. Additionally, the illustrated opening 113 is relatively large in comparison with the overall size of the plate 110. However, the opening 113 may be formed having any desired shape, location, and relative size. A locking member 114 is retained within the opening 113 for rotation or other movement relative to the plate 110. The illustrated locking member 114 has an enlarged central opening 114a formed therethrough. The inner surface of the enlarged central opening 114a may, if desired, be formed having one or more flats or other engagement structures provided thereon. The locking member 114 also has one or more locking arms 114b that extend outwardly therefrom. In the illustrated embodiment, the locking member 114 has four of such locking arms 114b provided thereon, one for each of the fasteners 112 provided within the fastener openings 111. However, the locking member 114 may be provided with a greater or lesser number of such locking arms 114b.

The locking member 114 may be moved relative to the plate 110 between a locked position (illustrated in FIGS. 16 and 17) and an unlocked position (illustrated in FIG. 18). In the unlocked position shown in FIGS. 16 and 17, the locking arms 114b do not extend over or within any portions of the fastener openings 111 formed through the plate 110. As a result, the fasteners 112 can be inserted within the fastener opening 111 prior to the installation of the third embodiment of the cervical plate assembly during a surgical procedure. Once the fasteners 112 have been inserted within the fastener openings 111, however, the locking member 114 can be moved to the locked position shown in FIG. 17, wherein portions of the locking arms 114b extend over the outer end surfaces 112a of the fasteners 112. As a result, the fasteners 112 are positively blocked by the locking arms 114b to prevent them from being removed from the fastener openings 111. The locking member 114 can be kept securely in this locked position by a friction fit or by other means, such as a detent (not shown). Such positive retention of the fasteners 112 to the plate 110 can facilitate the installation of the plate 110 in an orthopedic surgical procedure.

Movement of the locking member 114 between the locked and unlocked positions can be accomplished either manually or by a conventional tool (not shown). The flats or other engagement structures provided on the inner surface of the enlarged central opening 114a can facilitate the use of such a tool. The enlarged central opening 114a formed through the locking member 114 provides a viewing window that results in an unobstructed view of the vertebrae and the bone graft, which can also facilitate the installation of the plate 110 in an orthopedic surgical procedure.

Figure 19:
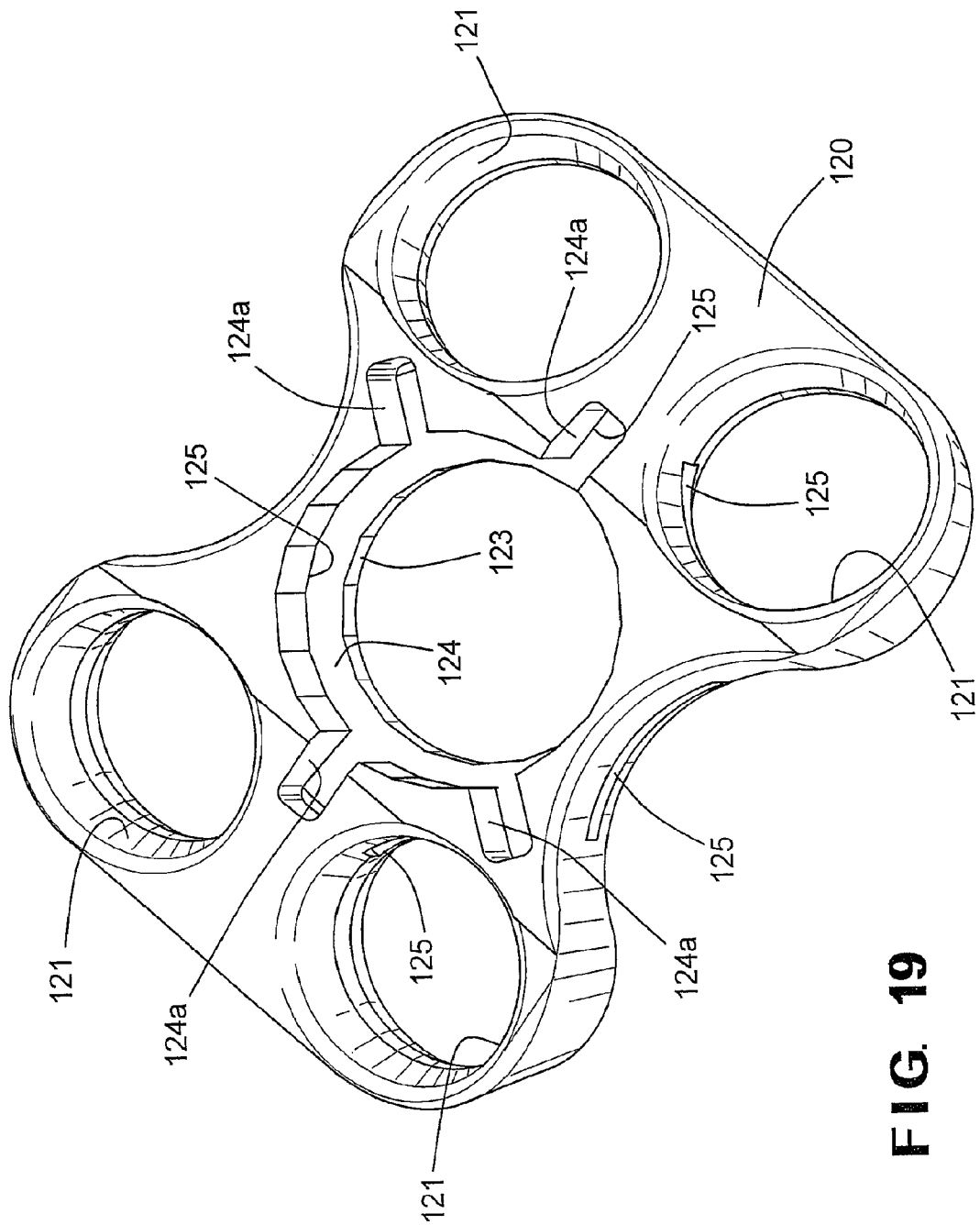
FIG. 19 is a perspective view of a portion of a fourth embodiment of a cervical plate assembly in accordance with this invention.
Figure 20:
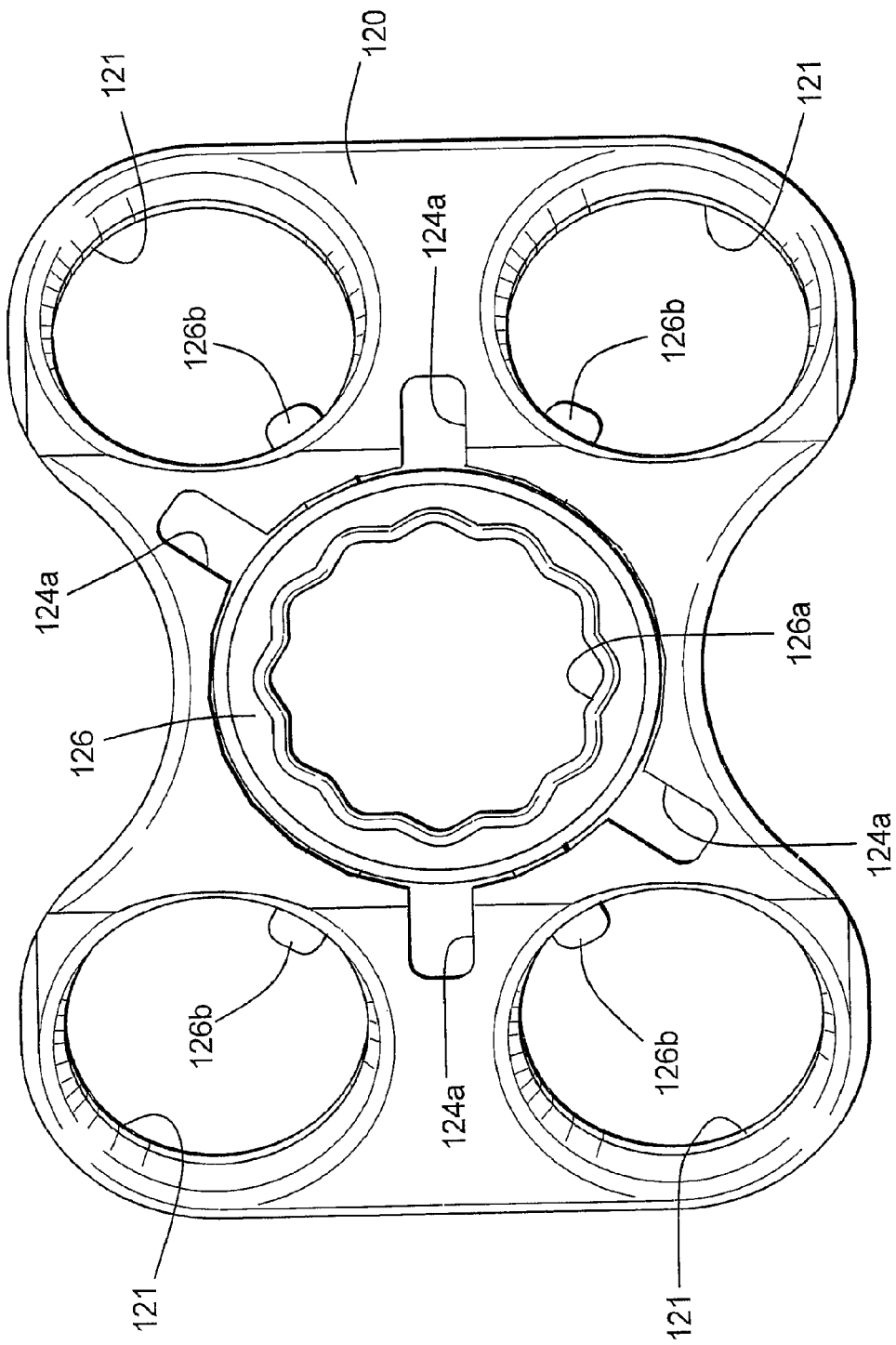
FIG. 20 is a top plan view of the fourth embodiment of the cervical plate assembly illustrated in FIG. 16 further including a locking member shown in a locked position.
Figure 21:
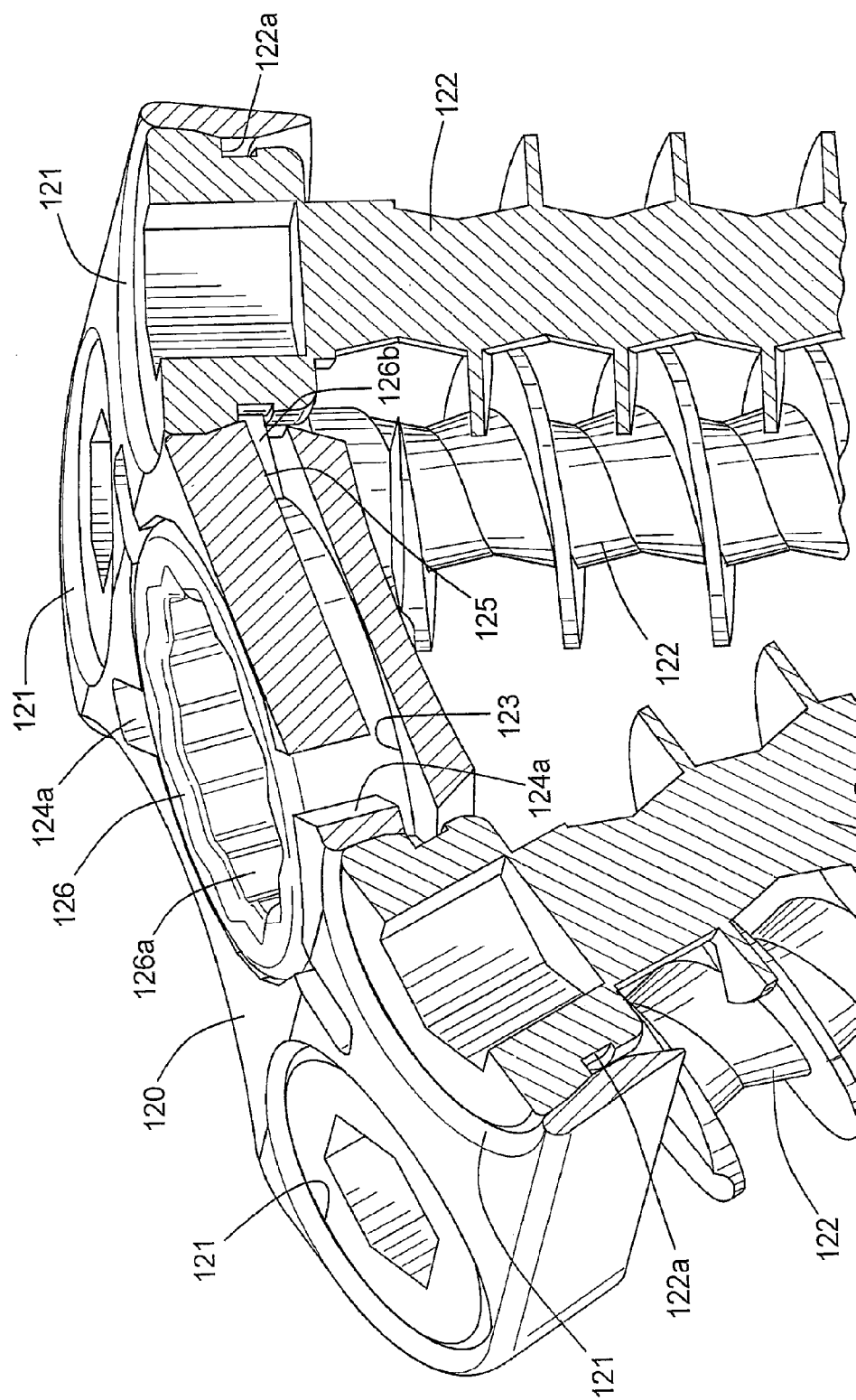
FIG. 21 is an enlarged perspective view, partially in cross section, of the fourth embodiment of the cervical plate assembly illustrated in FIGS. 19 and 20.

Referring now to FIGS. 19 through 21, a fourth embodiment of a cervical plate assembly in accordance with this invention is illustrated. The fourth embodiment of the cervical plate assembly includes a plate 120 that can be formed from any desired (preferably rigid) material, such as titanium, stainless steel, cobalt-chrome, or other medically-approved biomaterial. The plate 120 is generally flat and planar in shape and may, as illustrated, be gently curved from side to side and/or from end to end. First and second pairs of fastener openings 121 are formed through the plate 120. In the illustrated embodiment, the fastener openings 121 are located on the opposite sides of the plate 120. However, the fastener openings 121 may be formed through the plate 120 at any desired locations. Although two pairs of such fastener openings 121 are shown in the illustrated embodiment, it will be appreciated that a greater or lesser number of such fastener openings 121 may be provided as desired. Respective fasteners 122 (see FIG. 21) are provided within each of the fastener openings 121 to secure the fourth embodiment of the cervical plate assembly to one or more bones in a human body, such as a pair of vertebrae in a spine, in the manner described above. Each of the fasteners 122 includes a groove 122a formed in the head portion thereof.

An opening 123 is formed through the plate 120. In the illustrated embodiment, the opening 123 is generally circular in shape and is located at the center of the plate 120. Additionally, the illustrated opening 123 is relatively large in comparison with the overall size of the plate 120. However, the opening 123 may be formed having any desired shape, location, and relative size. As best shown at 124, a portion of the opening 123 is recessed. The illustrated recessed portion 124 extends about the opening 123 and includes one or more arm portions 124a, the purpose of which will be explained below. Additionally, the illustrated opening 123 includes one or more slots or undercut portions 125 that extend from the recessed portion 124 and the arm portions 124a and into the fastener openings 121. The purpose for the slots or undercut portions 125 will also be explained below.

As shown in FIGS. 20 and 21, a locking member 126 is retained within the opening 123 for rotation or other movement relative to the plate 120. The illustrated locking member 126 has an enlarged central opening 126a formed therethrough. The inner surface of the enlarged central opening 126a may, if desired, be formed having one or more flats or other engagement structures provided thereon for the same purpose as described above. The locking member 126 also has one or more locking arms 126b that extend outwardly therefrom. In the illustrated embodiment, the locking member 126 has four of such locking arms 126b provided thereon, one for each of the fasteners 126 provided within the fastener openings 121. However, the locking member 126 may be provided with a greater or lesser number of such locking arms 126b.

The locking member 126 may be installed on the plate 120 by initially disposing the arms 126b of the locking member 126 in alignment with the arm portions 124a of the recessed portion 124 of the opening 123, then moving the locking member 126 axially within the opening such that the arms 126b are received within the arm portions 124a of the recessed portion 124. Then, the locking member 126 may be moved relative to the plate 120 between a locked position (illustrated in FIGS. 20 and 21) and an unlocked position (not illustrated). In the unlocked position, the locking arms 126b do not extend within any portions of the fastener openings 121 formed through the plate 120. As a result, the fasteners 122 can be inserted within the fastener openings 121 prior to the installation of the fourth embodiment of the cervical plate assembly during a surgical procedure. Once the fasteners 122 have been inserted within the fastener openings 121, the locking member 126 can be moved to the locked position shown in FIGS. 20 and 21, wherein portions of the locking arms 126b extend within the grooves 122a provided in the head portions of the fasteners 122, as illustrated in FIG. 21. If desired, the locking arms 126b may extend into grooves that are located between the head portions of the fasteners 122 and the threads provided thereon or between ones of the threads themselves. As a result, the fasteners 122 are positively blocked by the locking arms 126b to prevent them from being removed from the fastener openings 121. Such positive retention of the fasteners 122 to the plate 120 can facilitate the installation of the plate 120 in an orthopedic surgical procedure.

Movement of the locking member 126 between the locked and unlocked positions can be accomplished either manually or by a conventional tool (not shown). The flats or other engagement structures provided on the inner surface of the enlarged central opening 126a can facilitate the use of such a tool. The enlarged central opening 126a formed through the locking member 126 provides a viewing window that results in an unobstructed view of the vertebrae and the bone graft. The enlarged central opening 126a can have any desired shape including, for example, hexagonal, octagonal, and the like. The locking member 126 can be kept securely in a locked position by a friction fit or by other means, such as a detent (not shown).

Figure 22:
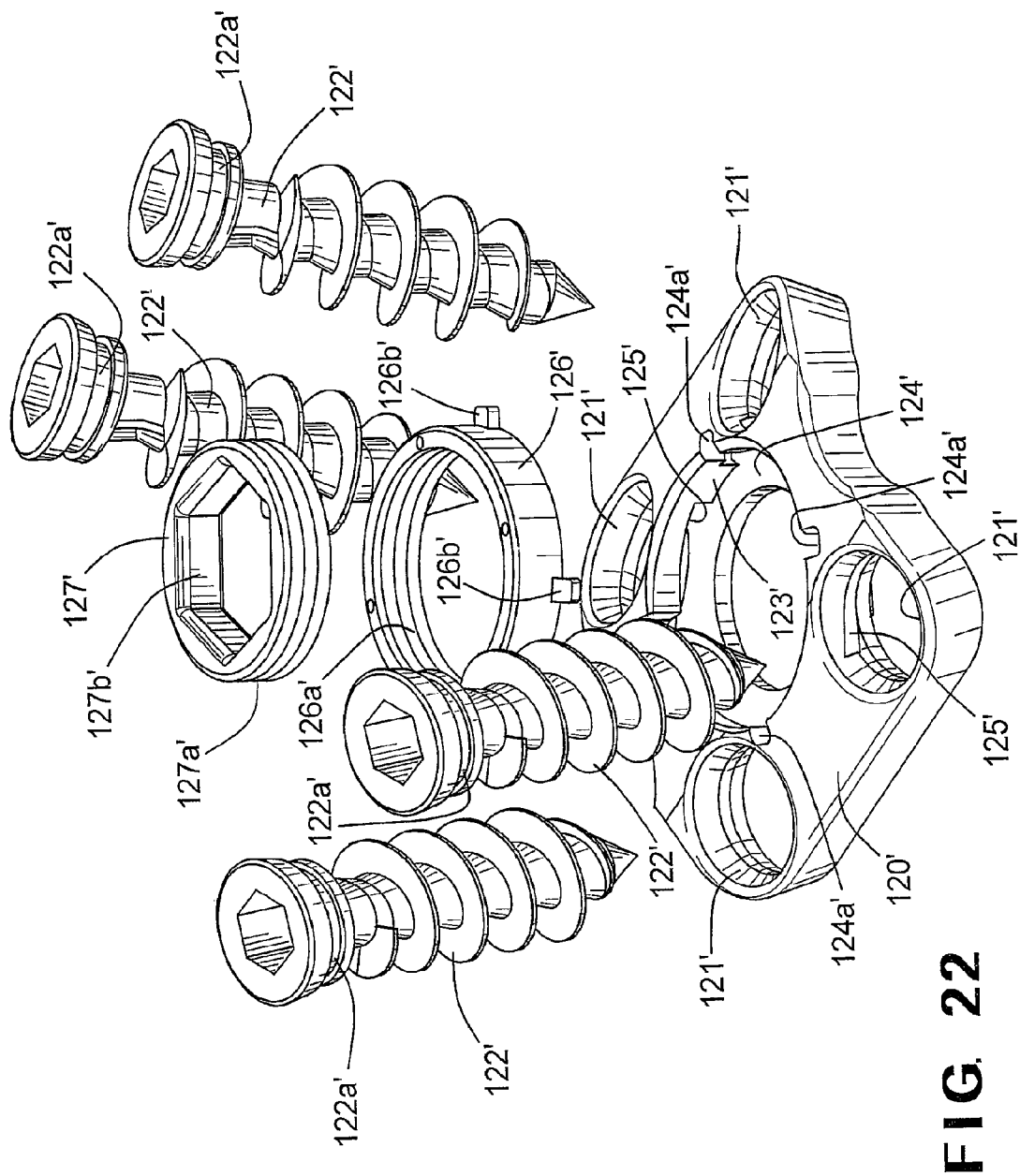
FIG. 22 is an exploded perspective view of a fifth embodiment of a cervical plate assembly in accordance with this invention.
Figure 23:
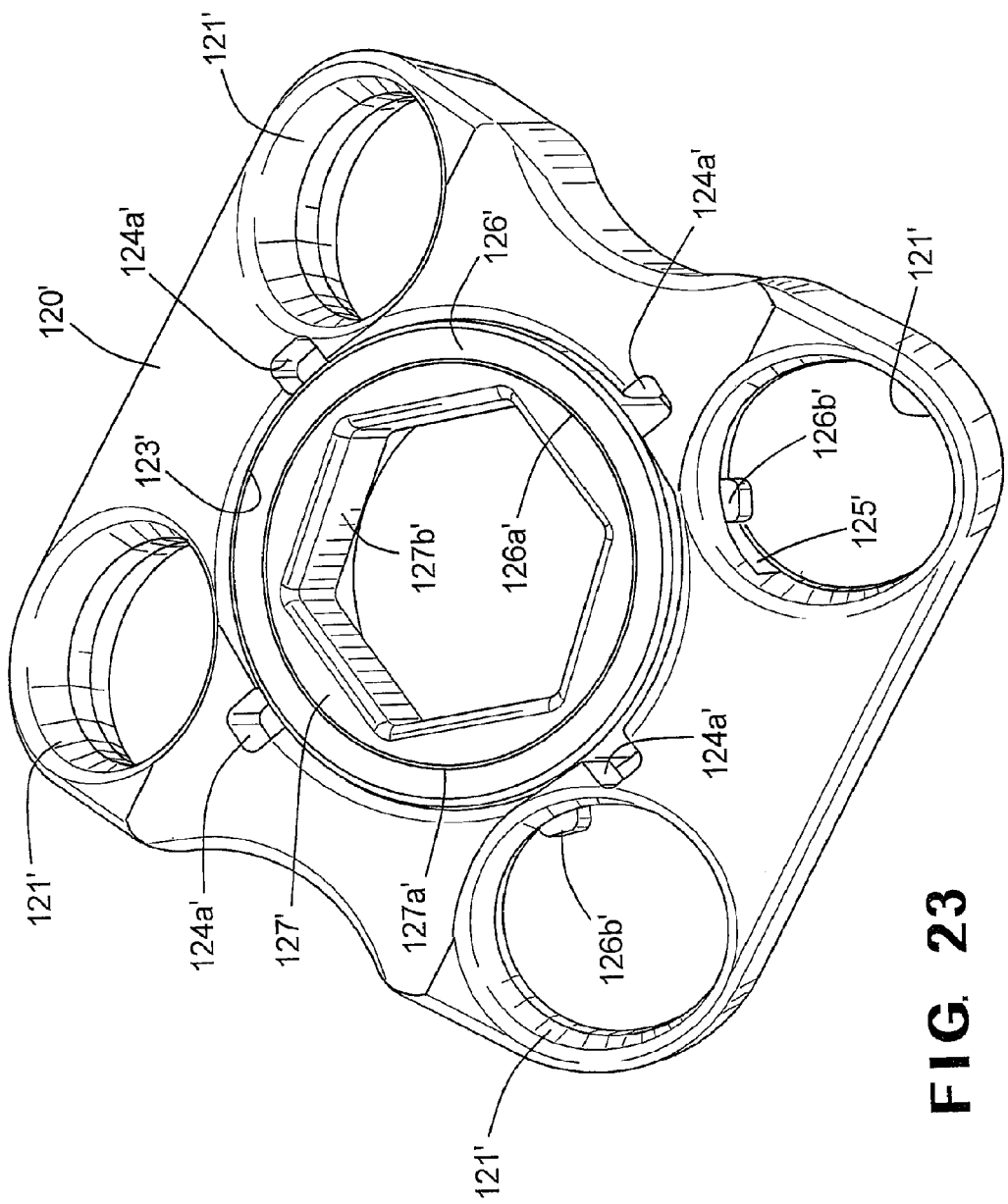
FIG. 23 is an enlarged perspective view of the fifth embodiment of the cervical plate assembly illustrated in FIG. 22.
Figure 24:
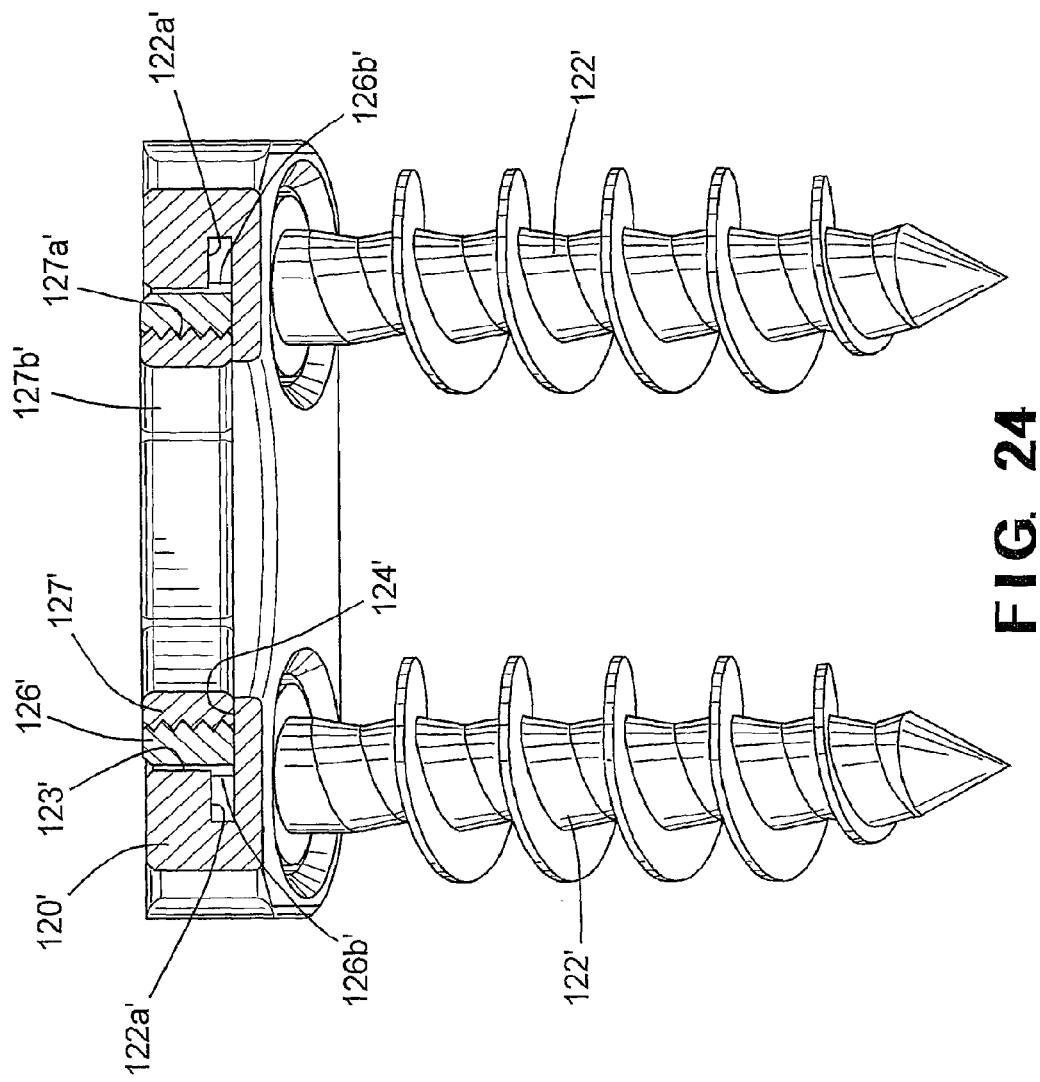
FIG. 24 is an enlarged sectional elevational view of the fifth embodiment of the cervical plate assembly illustrated in FIGS. 22 and 23.
Figure 25:
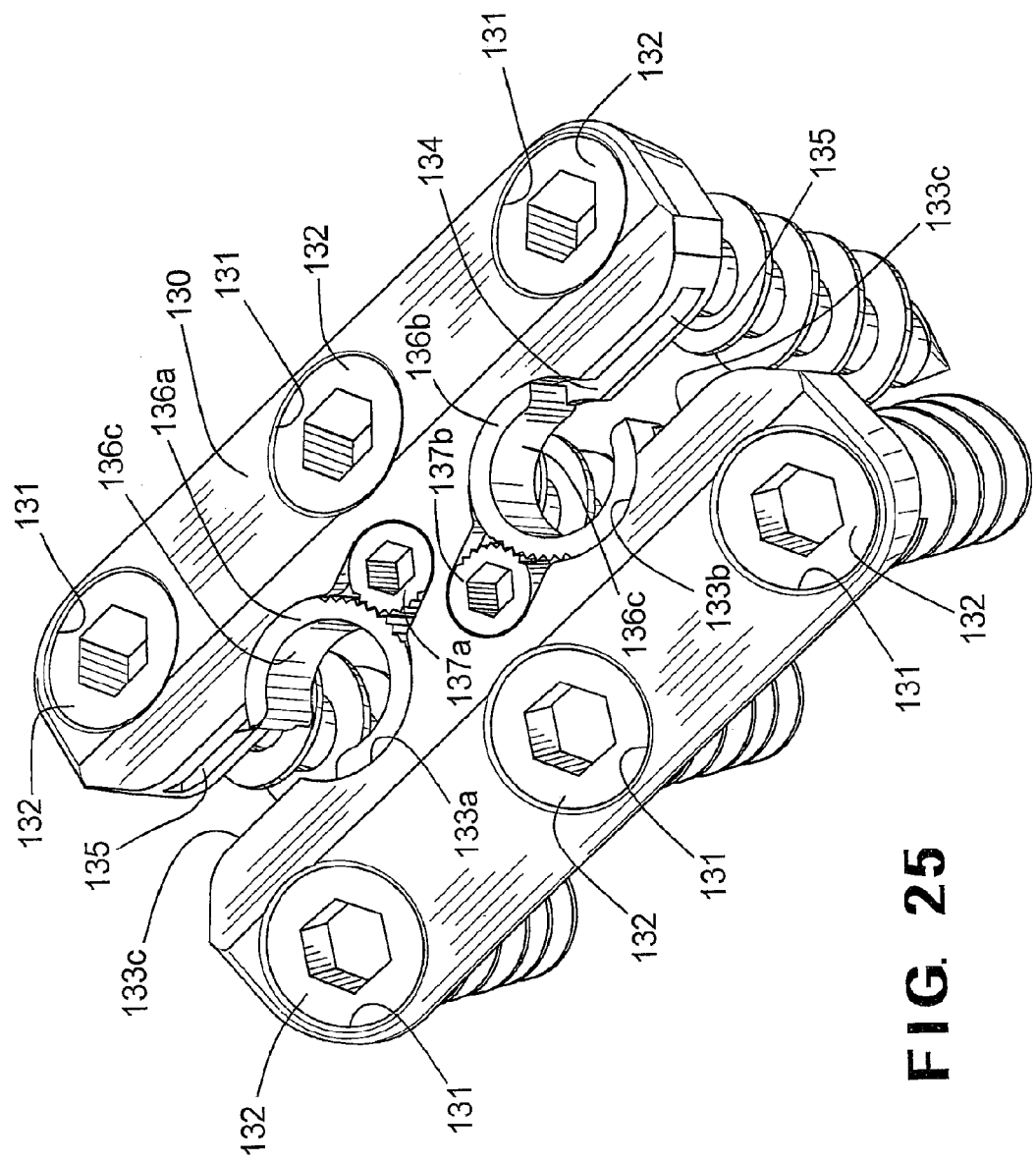
FIG. 25 is a perspective view of a sixth embodiment of a cervical plate assembly in accordance with this invention.

Referring now to FIGS. 22 through 24, a fifth embodiment of a cervical plate assembly in accordance with this invention is illustrated. The fifth embodiment of the cervical plate assembly is similar to the fourth embodiment of the cervical plate assembly described above, and like reference numbers are used to indicate similar parts. In this fifth embodiment of the cervical plate assembly, however, the inner surface of the enlarged central opening 126a' of the locking member 126' has a thread or other engagement structure provided thereon. Additionally, the fifth embodiment of the cervical plate assembly includes a jam screw 127'. The jam screw 127' includes an outer surface 127a' having a thread or other engagement structure provided thereon that is complementary to the thread provided on the inner surface of the enlarged central opening 126a' of the locking member 126'. As a result, the jam screw 127' can be screwed into the enlarged central opening 126a' of the locking member 126', as shown in FIG. 24. The illustrated jam screw 127' has an enlarged central opening 127b' formed therethrough. The inner surface of the enlarged central opening 127b' may, if desired, be formed having one or more flats or other engagement structures provided thereon for the same purpose as described above.

The fifth embodiment of the cervical plate assembly can be used to positively retain the fasteners 122' to the plate 120' and thereby facilitate the installation of the plate 120' in an orthopedic surgical procedure in the manner described above. Additionally, however, once the locking member 126' has been installed on the plate 120' and moved to the locked position, the jam screw 127' can be threaded within the locking member 126' (or tightened relative to the locking member 126' if pre-installed therein) such that the lower end of the jam screw 127' abuts the recessed area 124'. As a result, friction between the jam screw 127', the locking member 126', and the plate 120' serves to positively maintain the locking member 126' in the locked position. Otherwise, the fifth embodiment of the cervical plate assembly functions similarly to the fourth embodiment of the cervical plate assembly.

Referring now to FIGS. 25 through 28, a sixth embodiment of a cervical plate assembly in accordance with this invention is illustrated. The sixth embodiment of the cervical plate assembly includes a plate 130 that can be formed from any desired (preferably rigid) material, such as titanium, stainless steel, cobalt-chrome, or other medically-approved biomaterial. The plate 130 is generally flat and planar in shape and may, as illustrated, be gently curved from side to side and/or from end to end. Three pairs of fastener openings 131 are formed through the plate 130. In the illustrated embodiment, the fastener openings 131 are located on the opposite sides of the plate 130. However, the fastener openings 131 may be formed through the plate 130 at any desired locations. Although three pairs of such fastener openings 131 are shown in the illustrated embodiment, it will be appreciated that a greater or lesser number of such fastener openings 131 may be provided as desired. Respective fasteners 132 are provided within each of the fastener openings 131 to secure the sixth embodiment of the cervical plate assembly to one or more bones in a human body, such as a pair of vertebrae in a spine, in the manner described above. Each of the fasteners 132 includes a groove (not shown) formed in the head portion thereof, which grooves can be similar to the grooves 122a formed in the head portions of the fasteners 122 described above.

First and second openings 133a and 133b are formed through the plate 130. In the illustrated embodiment, the openings 133a and 133b are generally circular in shape and are located along a longitudinal axis defined by the plate 130. Additionally, the illustrated openings 133a and 133b are relatively large in comparison with the overall size of the plate 130. However, the openings 133a and 133b may be formed having any desired shapes, locations, and relative sizes. The illustrated openings 133a and 133b include respective side portions 133c that extend to the longitudinal ends of the plate 130 in order to accommodate extensions (not shown) that may be connected thereto. Such extensions can be generally similar in structure and operation to the illustrated plate 130 and, therefore, be used to secure the sixth embodiment of the cervical plate assembly to additional vertebrae. Portions of the openings 133a and 133b are recessed as shown at 134. The illustrated recessed portions 134 extend about the openings 133a and 133b. Additionally, the illustrated openings 133a and 133b include one or more slots or undercut portions 135 that extend from the recessed portions 134 and into the fastener openings 131. The purpose for the slots or undercut portions 135 will be explained below.

First and second locking members 136a and 136b are respectively retained within the openings 133a and 133b for rotation or other movement relative to the plate 130. Each of the illustrated locking members 136a and 136b has an enlarged central opening 136c formed therethrough. The locking members 136a and 136b also have one or more locking arms 136d that extend outwardly therefrom. In the illustrated embodiment, the first locking member 136a has four of such locking arms 136d provided thereon, while the second locking member 136b has two of such locking arms 136d provided thereon, (one for each of the fasteners 132 provided within the fastener openings 131). However, the locking members 136a and 136b may be provided with a greater or lesser number of such locking arms 136d. Additionally, each of the locking members 136*a* and 136*b* has an exterior surface that is provided with a plurality of teeth 136*e* or other actuating structures.

The first and second locking members 136*a* and 136*b* may be moved relative to the plate 130 between unlocked positions (illustrated in FIG. 27) and locked positions (illustrated in FIG. 28) by first and second actuators 137*a* and 137*b*. The first actuator 137*a* is supported on the plate 130 for rotation or other movement relative thereto and includes an exterior surface that is provided with a plurality of teeth 137*c* or other actuating structures that cooperate with the plurality of teeth 136*e* provided on the first locking member 136*a*. Similarly, the second actuator 137*b* is supported on the plate 130 for rotation or other movement relative thereto and includes an exterior surface that is provided with a plurality of teeth 137*c* or other actuating structures that cooperate with the plurality of teeth 136*e* provided on the second locking member 136*b*. Thus, rotation of the first and second actuators 137*a* and 137*b* causes corresponding rotation of the respective first and second locking members 136*a* and 136*b* between the unlocked and locked positions. Rotation of the first and second actuators 137*a* and 137*b* can be accomplished either manually or by a conventional tool (not shown). The enlarged central openings 136*c* formed through the members 136*a* and 136*b* provide viewing windows that results in an unobstructed view of the vertebrae and the bone graft. If desired, a single actuator may be used instead of two. This single actuator may lock up to eight of the fasteners 132 with a single turn by having interdigitating teeth on each side such that it controls the rotation of both of the first and second locking members 136*a* and 136*b*.

In the unlocked positions, the locking arms 136*d* do not extend within any portions of the fastener openings 131 formed through the plate 130. As a result, the fasteners 132 can be inserted within the fastener openings 131 of the sixth embodiment of the cervical plate assembly during a surgical procedure. Once the fasteners 132 have been inserted within the fastener openings 131, the locking members 136*a* and 136*b* can be moved to the locked positions, wherein portions of the locking arms 136*d* extend within the grooves provided in the head portions of the fasteners 132, as described above. As a result, the fasteners 132 are positively blocked by the locking arms 136*d* to prevent them from being removed from the fastener openings 131. Such positive retention of the fasteners 132 to the plate 130 can facilitate the installation of the plate 130 in an orthopedic surgical procedure.

Figure 26:
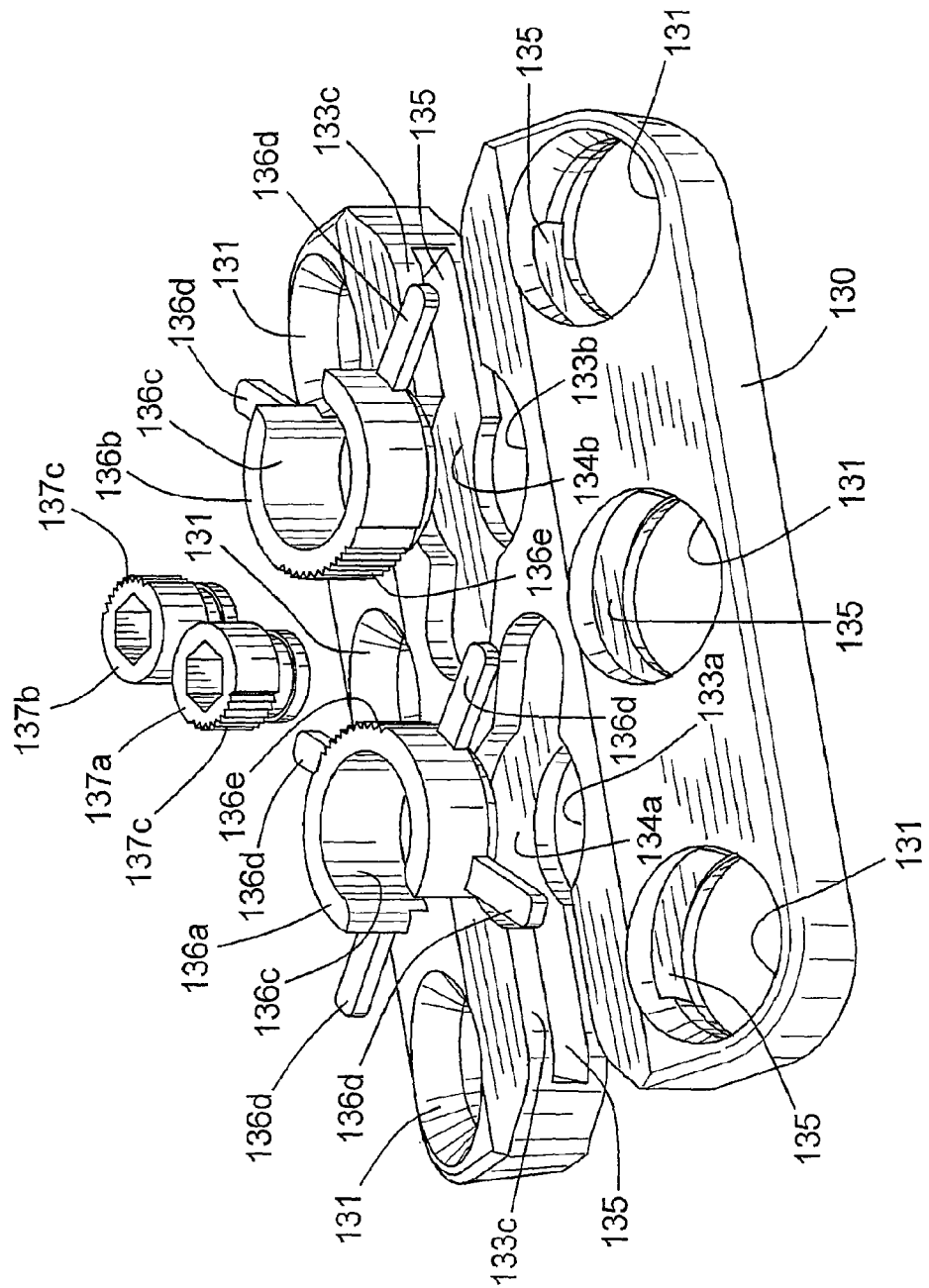
FIG. 26 is an exploded perspective view of the sixth embodiment of the cervical plate assembly illustrated in FIG. 25.
Figure 27:
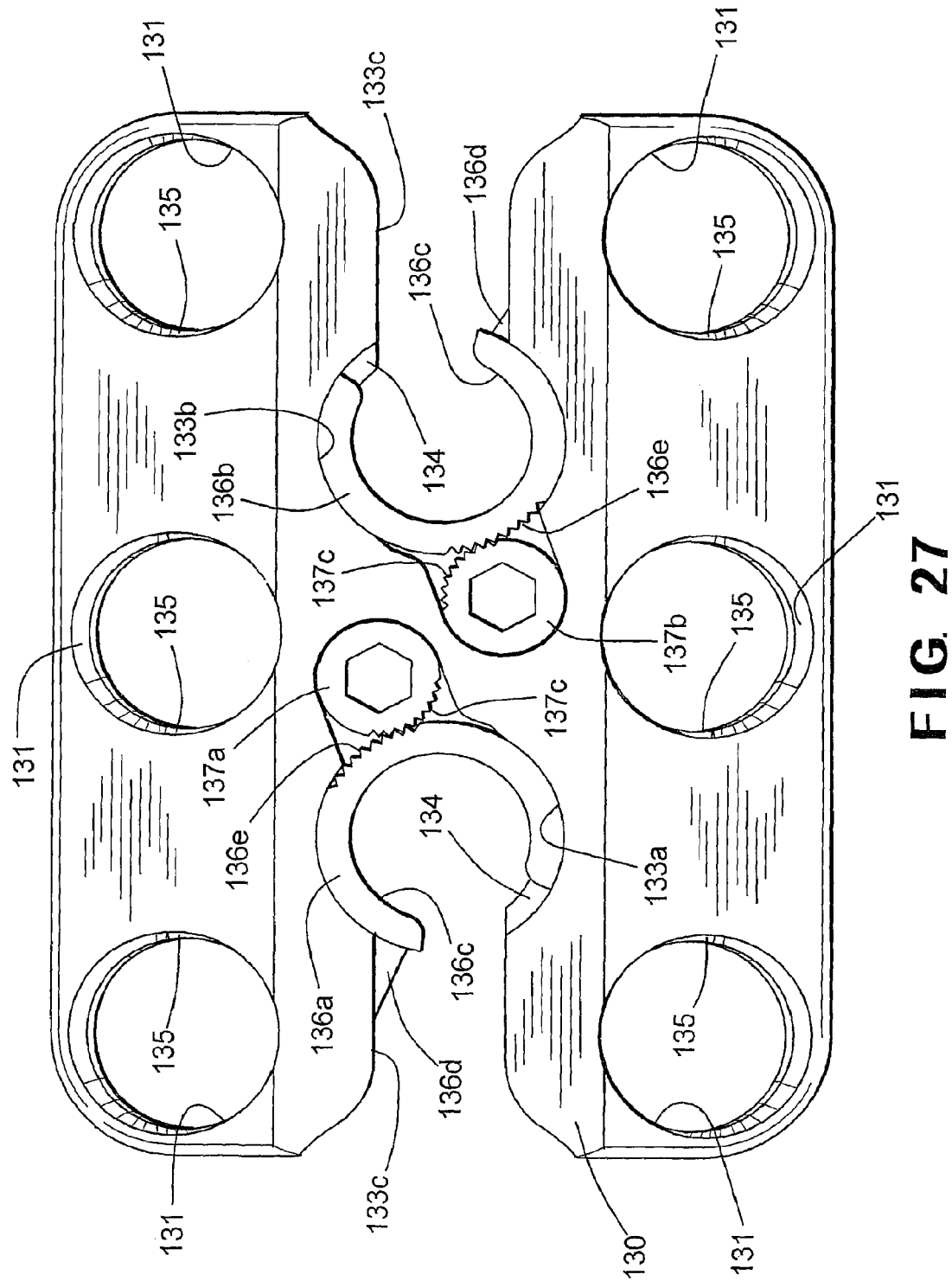
FIG. 27 is a top plan view of the sixth embodiment of the cervical plate assembly illustrated in FIGS. 24 and 25, wherein locking members are shown in unlocked positions.
Figure 28:
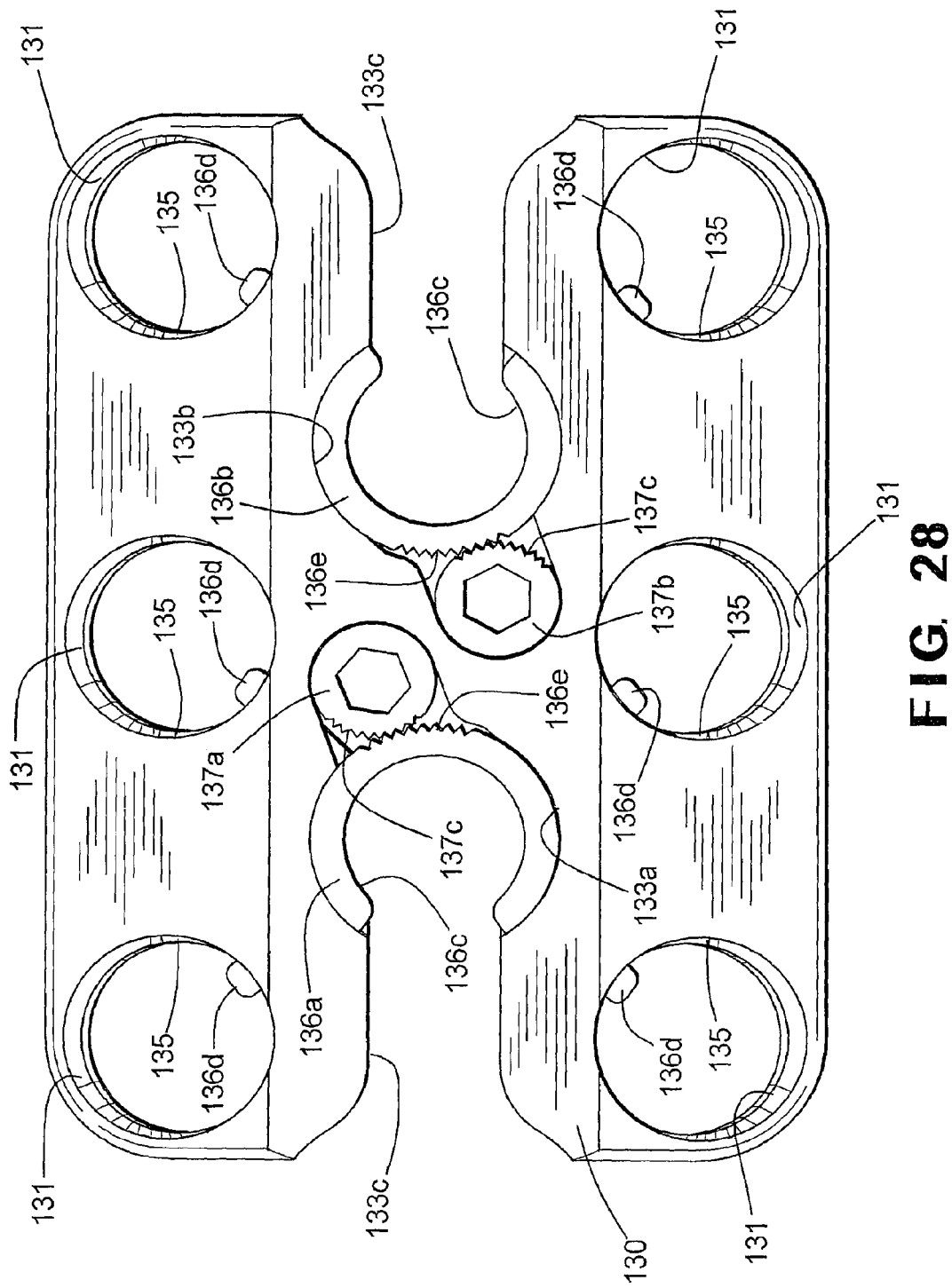
FIG. 28 is a top plan view similar to FIG. 27 wherein the locking members are shown in locked positions.
Figure 29:
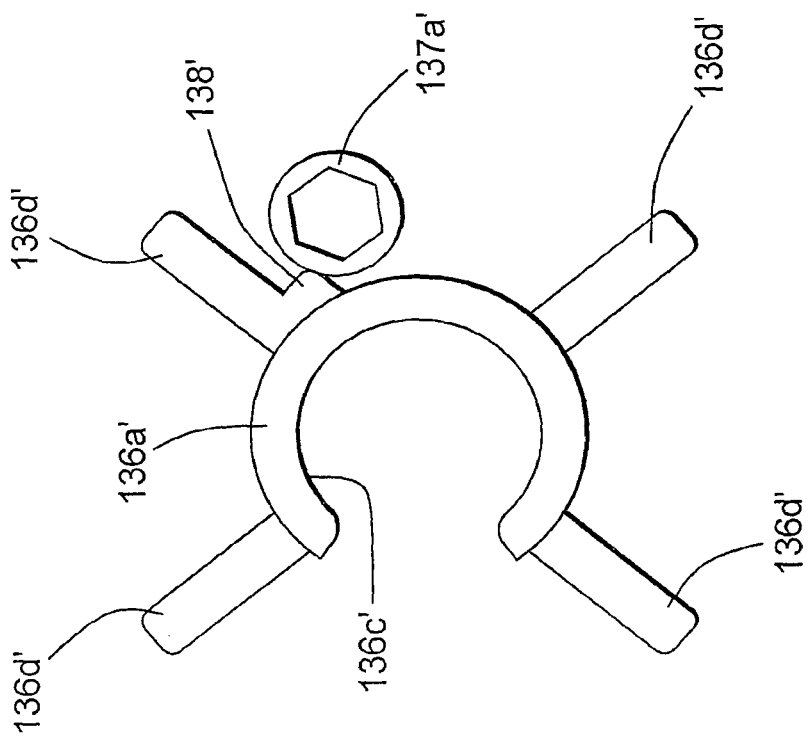
FIG. 29 is an enlarged top plan view of a first modified embodiment of a locking member that can be used with the sixth embodiment of the cervical plate assembly illustrated in FIGS. 25 through 28.

FIG. 29 is an enlarged top plan view of a first modified embodiment of a locking member 136*a*' that can be used with the sixth embodiment of the cervical plate assembly illustrated in FIGS. 25 through 28. The first modified locking member 136*a*' is similar to the locking member 136 described above, and like reference numbers are used to indicate similar parts. In this first modified locking member 136*a*', however, the plurality of teeth 136*e* provided on the first locking member 136*a* and the plurality of teeth 137*c* provided on the first actuator 137*a* have been omitted. Thus, the first modified locking member 136*a*' can be manually rotated between the unlocked and locked positions. A boss 138' is provided on one of the locking arms 136*d*'. As shown in FIG. 26, the boss 138' is engaged by the first actuator 137*a*' when the locking arm 136*d*' has been rotated to a desired position. The engagement of the boss 138' by the first actuator 137*a*' functions to retain the locking arm 136*d*' in the desired position. Otherwise, the first modified locking member 136*a*' functions similarly to the locking member 136*a*.

Figure 30:
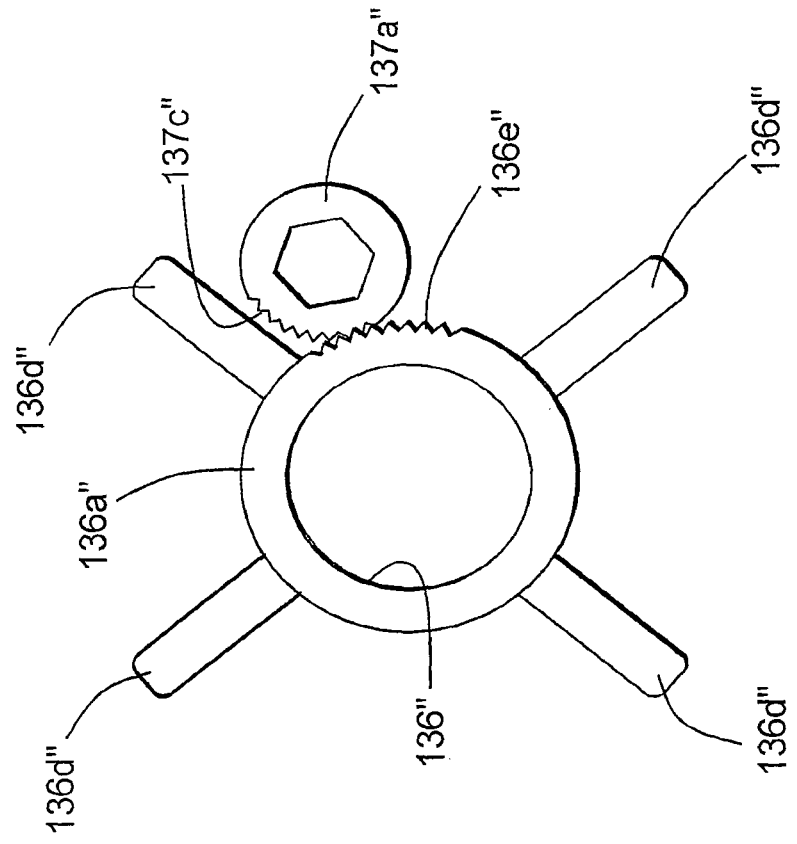
FIG. 30 is an enlarged top plan view of a second modified embodiment of a locking member that can be used with the sixth embodiment of the cervical plate assembly illustrated in FIGS. 25 through 28.

FIG. 30 is an enlarged top plan view of a second modified embodiment of a locking member that can be used with the sixth embodiment of the cervical plate assembly illustrated in FIGS. 22 through 25. The second modified locking member 136*a*" is similar to the locking member 136 described above, and like reference numbers are used to indicate similar parts. In this second modified locking member 136*a*", however, the body of the second modified locking member 136*a*" is completely circular. Otherwise, the second modified locking member 136*a*" functions similarly to the locking member 136*a*.

The principle and mode of operation of this invention have been explained and illustrated in its preferred embodiments. However, it must be understood that this invention may be practiced otherwise than as specifically explained and illustrated without departing from its spirit or scope.

What is claimed is:

1. A cervical plate assembly comprising:
   a plate having first and second openings formed therethrough;
   a first fastener extending through the first opening and adapted to be secured to a first vertebra;
   a second fastener extending through the second opening and adapted to be secured to a second vertebra;
   a locking member that selectively retains the first and second fasteners to the plate, the locking member having an engagement structure; and
   a jam screw having an engagement structure that cooperates with the engagement structure of the locking member such that movement of the jam screw relative to the locking member causes the locking member to engage the plate to prevent movement of the locking member relative to the plate; wherein
   the locking member is movable relative to the plate between a locked position, wherein the locking member retains the first and second fasteners to the plate, and an unlocked position, wherein the locking member does not retain the first and second fasteners to the plate; and wherein either:
   (1) the locking member is rotatable relative to the plate between the locked and unlocked positions;
   (2) portions of the locking member extend over outer end surfaces of the fasteners when in the locked position; or
   (3) portions of the locking member extend into grooves provided in the fasteners when in the locked position.

2. The cervical plate assembly defined in claim 1 wherein the locking member is rotatable relative to the plate between the locked and unlocked positions.

3. The cervical plate assembly defined in claim 1 wherein portions of the locking member extend over outer end surfaces of the fasteners when in the locked position.

4. The cervical plate assembly defined in claim 1 wherein portions of the locking member extend into grooves provided in the fasteners when in the locked position.

5. The cervical plate assembly defined in claim 1 wherein the locking member has an opening defined by an inner surface having the locking plate engagement structure provided thereon, and wherein the jam screw has an outer surface having the jam screw engagement structure provided thereon.

6. A cervical plate assembly comprising:
   a plate having first and second openings formed therethrough;
   a first fastener extending through the first opening and adapted to be secured to a first vertebra;
   a second fastener extending through the second opening and adapted to be secured to a second vertebra;
   a locking member that selectively retains the first and second fasteners to the plate, the locking member having an engagement structure; and a jam screw having an engagement structure that cooperates with the engagement structure of the locking member such that movement of the jam screw relative to the locking member causes the locking member to engage the plate to prevent movement of the locking member relative to the plate, wherein the locking member is rotatable relative to the plate between the locked and unlocked positions, and wherein the jam screw is rotatable relative to the locking member for selectively retaining the locking member in the locked position.

7. A cervical plate assembly comprising:

a plate having first and second openings formed therethrough;

a first fastener extending through the first opening and adapted to be secured to a first vertebra;

a second fastener extending through the second opening and adapted to be secured to a second vertebra;

a locking member that selectively retains the first and second fasteners to the plate, the locking member having an engagement structure; and a jam screw having an engagement structure that cooperates with the engagement structure of the locking member such that movement of the jam screw relative to the locking member causes the locking member to engage the plate to prevent movement of the locking member relative to the plate, wherein the locking plate engagement structure is a thread, and wherein the jam screw engagement structure is a thread that cooperates with the locking plate engagement thread.

8. A cervical plate assembly comprising:

a plate having first and second openings formed therethrough;

a first fastener extending through the first opening and adapted to be secured to a first vertebra;

a second fastener extending through the second opening and adapted to be secured to a second vertebra;

a locking member that selectively retains the first and second fasteners to the plate, the locking member having an engagement structure; and a jam screw having an engagement structure that cooperates with the engagement structure of the locking member such that movement of the jam screw relative to the locking member causes the locking member to engage the plate to prevent movement of the locking member relative to the plate; wherein the plate has a slot formed therein, and wherein the locking member has first and second locking arms that are received within the slot when the locking member retains the first and second fasteners to the plate, and wherein movement of the jam screw relative to the locking member causes the locking arms of the locking member to engage the portions of the plate defining the slot to prevent movement of the locking member relative to the plate.

* * * * *